US007635559B2

(12) United States Patent
Lee et al.

(10) Patent No.: US 7,635,559 B2
(45) Date of Patent: Dec. 22, 2009

(54) POLYNUCLEOTIDE ASSOCIATED WITH A TYPE II DIABETES MELLITUS COMPRISING SINGLE NUCLEOTIDE POLYMORPHISM, MICROARRAY AND DIAGNOSTIC KIT COMPRISING THE SAME AND METHOD FOR ANALYZING POLYNUCLEOTIDE USING THE SAME

(75) Inventors: Kyu-Sang Lee, Suwon-si (KR);
Jae-Heup Kim, Seoul (KR);
Kyung-Hee Park, Seoul (KR); Yeon-Su Lee, Goyang-si (KR); Ok-Kyoung Son, Seoul (KR); Ji-Young Cho, Daejeon-si (KR); Yeon-A Park, Yongin-si (KR);
Sung-Woo Hong, Yongin-si (KR);
Jung-Joo Hwang, Suwon-si (KR);
Hyo-Jeong Jeon, Anyang-si (KR)

(73) Assignee: Samsung Electronics Co., Ltd. (KR)

( * ) Notice: Subject to any disclaimer, the term of this patent is extended or adjusted under 35 U.S.C. 154(b) by 251 days.

(21) Appl. No.: 10/546,685

(22) PCT Filed: Dec. 24, 2004

(86) PCT No.: PCT/KR2004/003441

§ 371 (c)(1),
(2), (4) Date: Aug. 23, 2005

(87) PCT Pub. No.: WO2005/061711

PCT Pub. Date: Jul. 7, 2005

(65) Prior Publication Data

US 2006/0216712 A1 Sep. 28, 2006

(30) Foreign Application Priority Data

Dec. 24, 2003 (KR) ...................... 10-2003-0096191
Dec. 23, 2004 (KR) ...................... 10-2004-0111102

(51) Int. Cl.
*C12Q 1/68* (2006.01)
*C12M 1/34* (2006.01)
(52) U.S. Cl. ........................................ 435/6; 435/287.1
(58) Field of Classification Search ........................ None
See application file for complete search history.

(56) References Cited

U.S. PATENT DOCUMENTS 5,474,796 A * 12/1995 Brennan ...................... 427/2.13

FOREIGN PATENT DOCUMENTS

| WO | WO 95/11995 | * | 5/1995 |
| WO | WO 97/22694 | A2 | 6/1997 |
| WO | WO 99/23217 | A1 | 5/1999 |
| WO | WO 02/12280 | * | 2/2002 |
| WO | WO 03/033513 | A1 | 4/2003 |
| WO | 03079747 | A2 | 10/2003 |

OTHER PUBLICATIONS

GenBank Accession No. AC008630.4 (pp. 1-3).*
Hattersley et al. ,Lancet, 2005, vol. 366, pp. 1315-1323.*
Ionnidis, Plost Med, 2005, 2(8):e124.*
Hegele, Arterioscler. Thromb. Vasc. Biol. 2002, 22:1058-1061.*
Barroso et al. ,Diabetic Medicine 2005, 22 :517-535.*
Mummidi et al. , J. Biol. Chem, 2002, vol. 273, pp. 18946-18961.*
Nikoloff et al. The Pharmacogenomics Journal, 2002, vol. 2, pp. 400-407.*
Reference SNP Cluster Report: rs1990936, available at www.ncbi.nlm.nih.gov/snp/snp_ref.cgi?rs=1990936, pp. 1-3.*
GenBank Accession No. AC008630.4, Dec. 19, 2000, pp. 1-3.*
Reference SNP Cluster Report: rs1990936, available at www.ncbi.nlm.nih.gov/snp/snp_ref.cgi?rs=1990936, printed Oct. 8, 2008.*
Gudayol, Monica et al., "Detection of a New Variant of the Mitochondrial Glycerol-3-phosphate Dehydrogenase Gene in Spanish Type 2 DM Patients," *Biochemical and Biophysical Research Communications* (1999) 263: 439-445.
Gusella, J.F., "DNA Polymorphism And Human Disease," *Ann. Rev. Biochem.* (1986) 55: 831-54.
Kwoh, D. Y. et al., "Transcription-based amplification system and detection of amplified human immunodeficiency virus type 1 with a bead-based sandwich hybridization format," *Proc. Natl. Acad. Sci. USA* (1989) 86:1173-1177.
Landegren, Ulf et al., "A Ligase-Mediated Gene Detection Technique," *Science* (1988) 241: 1077-1080.
Nielsen, Peter E. et al., "Sequence-Selective Recognition of DNA by Strand Displacement with a Thymine-Substituted Polyamide," *Science* (1991) 254: 1497-1500.
Wu, Dan Y. and Wallace, Bruce R., "The Ligation Amplification Reaction (LAR)-Amplification of Specific DNA Sequences Using Sequential Rounds of Template-Dependent Ligation," *Genomics* (1989) 4: 560-569.
International Search Report for International Application No. PCT/KR2004/003441, Mailed Feb. 25, 2005.
Written Opinion for International Application No. PCT/KR2004/003441, Mailed Feb. 25, 2005.
Hara, K., et al.; "Genetic Variation in the Gene Encoding Adiponectin Is Associated With an Increased Risk of Type 2 Diabetes in the Japanese Population"; Diabetes; vol. 51; pp. 536-540; Feb. 2002.
Busch, C.P., et al.; "Genetic determinants of type 2 diabetes mellitus"; Clin. Genet.; vol. 60; pp. 243-254; 2001.
Sesti, G.; "Insulin receptor substrate polymorphisms and Type 2 diabetes mellitus"; Pharmacogenomics; vol. 1, No. 3; pp. 343-357; 2000.
Sakurai, K., et al; "Mutations in the Hepatocyte Nuclear Factor-4alpha Gene in Japanese with Non-insulin-Dependent Diabetes: A Nucleotide Substitution in the Polypyrimidine Tract on Intron 1b"; Hormone and Metabolic Research; vol. 32; pp. 316-320; 2000.
European Search Report dated Feb. 14, 2008 for Application No. 04808570.8 (All references listed above are those cited in the Search Report and not previously submitted via IDS).

* cited by examiner

*Primary Examiner*—Sarae Bausch
(74) *Attorney, Agent, or Firm*—Cantor Colburn LLP

(57) ABSTRACT

Provided is a polynucleotide for diagnosis or treatment of type II diabetes mellitus, including at least 10 contiguous nucleotides of a nucleotide sequence selected from the group consisting of nucleotide sequences of SEQ ID NOS: 1-80 and including a nucleotide at position 101 of the nucleotide sequence, or a complementary polynucleotide thereof.

3 Claims, No Drawings

SEQUENCE LISTING

<160> NUMBER OF SEQ ID NOS: 200

<210> SEQ ID NO 1
<211> LENGTH: 201
<212> TYPE: DNA
<213> ORGANISM: Homo sapiens

<400> SEQUENCE: 1

```
taaaaacaga tgggtgatcc cagtcctcta aatataatcg gggatgccaa atcttttcaa      60
agagaattca tatatacaac ttaaaggcca aggagcccaa ctcaatcaaa atttgagcca     120
ggatatgcta agttcaatca gcttgaatat gggcaaagtg taagacctag ccagcacttc     180
agatatatac agagaaccac a                                              201
```

<210> SEQ ID NO 2
<211> LENGTH: 201
<212> TYPE: DNA
<213> ORGANISM: Homo sapiens

<400> SEQUENCE: 2

```
taaaaacaga tgggtgatcc cagtcctcta aatataatcg gggatgccaa atcttttcaa      60
agagaattca tatatacaac ttaaaggcca aggagcccaa ttcaatcaaa atttgagcca     120
ggatatgcta agttcaatca gcttgaatat gggcaaagtg taagacctag ccagcacttc     180
agatatatac agagaaccac a                                              201
```

<210> SEQ ID NO 3
<211> LENGTH: 201
<212> TYPE: DNA
<213> ORGANISM: Homo sapiens

<400> SEQUENCE: 3

```
gtctgttttt catgggataa ttttattga tctatatcca aattgaattt gaatatactt      60
tattcctatg taatctcctt tgtcctctca aagacattta attttttttt ccaatactgt    120
attttccgt cctaaaattt ccatttgttt cttttatagt ttttatttta ttgctgagat     180
acttctatca tgtctttcac c                                              201
```

<210> SEQ ID NO 4
<211> LENGTH: 201
<212> TYPE: DNA
<213> ORGANISM: Homo sapiens

<400> SEQUENCE: 4

```
gtctgttttt catgggataa ttttattga tctatatcca aattgaattt gaatatactt      60
tattcctatg taatctcctt tgtcctctca aagacattta gttttttttt ccaatactgt    120
attttccgt cctaaaattt ccatttgttt cttttatagt ttttatttta ttgctgagat     180
acttctatca tgtctttcac c                                              201
```

<210> SEQ ID NO 5
<211> LENGTH: 201
<212> TYPE: DNA
<213> ORGANISM: Homo sapiens

<400> SEQUENCE: 5

```
gcagcagtac ggacgttaca ggaaagccat tgctagctct gctcctttaa catgtgtaaa      60
aacatctgtg ggtgacaggc agcaccccag ctcctgggt agtgacagag ctctcagga     120
```

```
ctccttccta ttgagatgca cagtggtcta ggtgttcccc aggcaggaac ctgtggaatc    180
tttggctttt ccttgaccta g                                              201

<210> SEQ ID NO 6
<211> LENGTH: 201
<212> TYPE: DNA
<213> ORGANISM: Homo sapiens

<400> SEQUENCE: 6
gcagcagtac ggacgttaca ggaaagccat tgctagctct gctcctttaa catgtgtaaa    60
aacatctgtg ggtgacaggc agcacccag ctcctggggt ggtgacagag gctctcagga    120
ctccttccta ttgagatgca cagtggtcta ggtgttcccc aggcaggaac ctgtggaatc    180
tttggctttt ccttgaccta g                                              201

<210> SEQ ID NO 7
<211> LENGTH: 201
<212> TYPE: DNA
<213> ORGANISM: Homo sapiens

<400> SEQUENCE: 7
aaaacaagac ttccagcgtt ttggtttgag caactgagtg gatgccagca ctgtttcctg    60
aaatgaataa gcctgggaga agtacaagtc aaaggggagg ggaggtgtta aaattgatca    120
agaactctat tttggacatg ttagtttgac atgttgatta aacgtccaag aggaaaagtc    180
acaaagccag tgagctatgg t                                              201

<210> SEQ ID NO 8
<211> LENGTH: 201
<212> TYPE: DNA
<213> ORGANISM: Homo sapiens

<400> SEQUENCE: 8
aaaacaagac ttccagcgtt ttggtttgag caactgagtg gatgccagca ctgtttcctg    60
aaatgaataa gcctgggaga agtacaagtc aaaggggagg agaggtgtta aaattgatca    120
agaactctat tttggacatg ttagtttgac atgttgatta aacgtccaag aggaaaagtc    180
acaaagccag tgagctatgg t                                              201

<210> SEQ ID NO 9
<211> LENGTH: 201
<212> TYPE: DNA
<213> ORGANISM: Homo sapiens

<400> SEQUENCE: 9
aaactgttca gtaatcctta atgtctagtt ctttccccaa agtacaattg cctgagtaaa    60
ttatcatagg taactttgag aaggaactat gataatcatg ttatataatg aggacttttc    120
tacaaggatt caggtacctc ttcaatgagt tctagatcta gaaactgaca caagtttggg    180
aactaggcaa gaaattgtga c                                              201

<210> SEQ ID NO 10
<211> LENGTH: 201
<212> TYPE: DNA
<213> ORGANISM: Homo sapiens

<400> SEQUENCE: 10
aaactgttca gtaatcctta atgtctagtt ctttccccaa agtacaattg cctgagtaaa    60
```

```
ttatcatagg taactttgag aaggaactat gataatcatg gtatataatg aggactttc      120 tacaaggatt caggtacctc ttcaatgagt tctagatcta gaaactgaca caagtttggg     180
aactaggcaa gaaattgtga c                                               201

<210> SEQ ID NO 11
<211> LENGTH: 201
<212> TYPE: DNA
<213> ORGANISM: Homo sapiens

<400> SEQUENCE: 11
tggagggtgg cagggagctg gaggagcagt gaggacttgc ttgagcagtc ttgacaagat      60
gtggcaggcc cacagccttc actgcctcta ggcccctga atgggtcact gtggttcctt     120
cagacacaag agagacccct tattgcccca gtcccactga cagactctgc ctcccaggcc    180
cactggccct gcccagacat g                                              201

<210> SEQ ID NO 12
<211> LENGTH: 201
<212> TYPE: DNA
<213> ORGANISM: Homo sapiens

<400> SEQUENCE: 12
tggagggtgg cagggagctg gaggagcagt gaggacttgc ttgagcagtc ttgacaagat      60
gtggcaggcc cacagccttc actgcctcta ggcccctga gtgggtcact gtggttcctt     120
cagacacaag agagacccct tattgcccca gtcccactga cagactctgc ctcccaggcc    180
cactggccct gcccagacat g                                              201

<210> SEQ ID NO 13
<211> LENGTH: 201
<212> TYPE: DNA
<213> ORGANISM: Homo sapiens

<400> SEQUENCE: 13
ccaggattag aatccaggtt ttctgaatca tggttcacta ccctcagtga ctgaaataaa      60
tagtgatatt agccaataag aaacctcagg agaggatcca cctaaagaa taccttttaca   120 gccacagtta ctcaagtcac ttgtttgtcc actcaattac tcagtattta ctgagttcct    180
gttaaaggca ctgggctaag t                                              201

<210> SEQ ID NO 14
<211> LENGTH: 201
<212> TYPE: DNA
<213> ORGANISM: Homo sapiens

<400> SEQUENCE: 14
ccaggattag aatccaggtt ttctgaatca tggttcacta ccctcagtga ctgaaataaa      60
tagtgatatt agccaataag aaacctcagg agaggatcca gcctaaagaa taccttttaca  120 gccacagtta ctcaagtcac ttgtttgtcc actcaattac tcagtattta ctgagttcct    180
gttaaaggca ctgggctaag t                                              201

<210> SEQ ID NO 15
<211> LENGTH: 201
<212> TYPE: DNA
<213> ORGANISM: Homo sapiens

<400> SEQUENCE: 15
taacaactta ccagttacta tattgacatt tatcaagtat tttctggagg tgatgcctta     60
```

```
gttgaaagat gagggaaaag ggaacatttc aggtataaag acaggcgaga caggaagact    120
acagggcagg gagcctttcg cttccctaaa aactgcactg cagctgcaca aatcccatta    180
ctctgtcttc atgtatagga t                                              201

<210> SEQ ID NO 16
<211> LENGTH: 201
<212> TYPE: DNA
<213> ORGANISM: Homo sapiens

<400> SEQUENCE: 16
taacaactta ccagttacta tattgacatt tatcaagtat tttctggagg tgatgcctta    60
gttgaaagat gagggaaaag ggaacatttc aggtataaag ccaggcgaga caggaagact    120
acagggcagg gagcctttcg cttccctaaa aactgcactg cagctgcaca aatcccatta    180
ctctgtcttc atgtatagga t                                              201

<210> SEQ ID NO 17
<211> LENGTH: 201
<212> TYPE: DNA
<213> ORGANISM: Homo sapiens

<400> SEQUENCE: 17
tgttttaagt tctcacccttt cccatgatgc aacagagaca actatgtcag aattcagaaa   60
aacaaagatg aaaatgtaat atccatgaag aataagacaa atcaaattat atcatacctg    120
aaagaaacgg aattttgttt ttaaggcaaa caagatccag cagatataat ttttggctct    180
tttgccacat acaaatcact a                                              201

<210> SEQ ID NO 18
<211> LENGTH: 201
<212> TYPE: DNA
<213> ORGANISM: Homo sapiens

<400> SEQUENCE: 18
tgttttaagt tctcacccttt cccatgatgc aacagagaca actatgtcag aattcagaaa   60
aacaaagatg aaaatgtaat atccatgaag aataagacaa gtcaaattat atcatacctg    120
aaagaaacgg aattttgttt ttaaggcaaa caagatccag cagatataat ttttggctct    180
tttgccacat acaaatcact a                                              201

<210> SEQ ID NO 19
<211> LENGTH: 201
<212> TYPE: DNA
<213> ORGANISM: Homo sapiens

<400> SEQUENCE: 19
cacaacccac tgacctcagg tagacctgtg tgtgcctacc tgggcctctg cctacctggt    60
ttctcttctc tatttycttg ttagaggatc ccactcacct tgatatgtct gctcctggaa    120
cctgtccctt ggaatcaagg attctgaaga tccaggcctc ttaggcttat ctccactccc    180
ccagtggccc tctgctgccc c                                              201

<210> SEQ ID NO 20
<211> LENGTH: 201
<212> TYPE: DNA
<213> ORGANISM: Homo sapiens

<400> SEQUENCE: 20
```

```
cacaacccac tgacctcagg tagacctgtg tgtgcctacc tgggcctctg cctacctggt      60
ttctcttctc tattttcttg ttagaggatc ccactcacct cgatatgtct gctcctggaa     120
cctgtccctt ggaatcaagg attctgaaga tccaggcctc ttaggcttat ctccactccc     180
ccagtggccc tctgctgccc c                                                201

<210> SEQ ID NO 21
<211> LENGTH: 201
<212> TYPE: DNA
<213> ORGANISM: Homo sapiens

<400> SEQUENCE: 21
ggcaagagcg agttggaatc caccccacac aatcccactg ttgcttctag gctctggcac      60
tcagaagccc accactgaga tgggcacaga gaaccctcaa gccaggagcc aaagcaggcc     120
tgagtggggg gtggagtttg gattttatg tatgtgtctg ggggacgggg tctgcacagg     180
ctttgcagac ccagcccagg c                                                201

<210> SEQ ID NO 22
<211> LENGTH: 201
<212> TYPE: DNA
<213> ORGANISM: Homo sapiens

<400> SEQUENCE: 22
ggcaagagcg agttggaatc caccccacac aatcccactg ttgcttctag gctctggcac      60
tcagaagccc accactgaga tgggcacaga gaaccctcaa cccaggagcc aaagcaggcc     120
tgagtggggg gtggagtttg gattttatg tatgtgtctg ggggacgggg tctgcacagg     180
ctttgcagac ccagcccagg c                                                201

<210> SEQ ID NO 23
<211> LENGTH: 201
<212> TYPE: DNA
<213> ORGANISM: Homo sapiens

<400> SEQUENCE: 23
gtgaagcggc agctgaggag acttcagtgc tcgccatggc cgacgaaaag cccaaggaag      60
gagtcaagac agaacaacga tcatattaat ttgaaggtgg tggggcagga tggttctatg     120
gtgcagttta agattaagag gcatacacca ctcagtaaac taatgaaagc ctattgtgaa     180
caacagggat tgtcaatgag g                                                201

<210> SEQ ID NO 24
<211> LENGTH: 201
<212> TYPE: DNA
<213> ORGANISM: Homo sapiens

<400> SEQUENCE: 24
gtgaagcggc agctgaggag acttcagtgc tcgccatggc cgacgaaaag cccaaggaag      60
gagtcaagac agaacaacga tcatattaat ttgaaggtgg cggggcagga tggttctatg     120
gtgcagttta agattaagag gcatacacca ctcagtaaac taatgaaagc ctattgtgaa     180
caacagggat tgtcaatgag g                                                201

<210> SEQ ID NO 25
<211> LENGTH: 201
<212> TYPE: DNA
<213> ORGANISM: Homo sapiens

<400> SEQUENCE: 25
```

```
ggggtctggg gagcagagaa accaggcatc tgtgagagag aaaaattagg acggacagag      60
aggagcacag aggaggggtg cagggagagt ccaggggggct ccattcctcc tccagctatt    120
tatgtcttca ggcccaggtg cttcctacct atgggttctc caggttatcc ttgtgtcctc    180
tccttgtata aactccctct t                                               201
```

<210> SEQ ID NO 26
<211> LENGTH: 201
<212> TYPE: DNA
<213> ORGANISM: Homo sapiens

<400> SEQUENCE: 26

```
ggggtctggg gagcagagaa accaggcatc tgtgagagag aaaaattagg acggacagag      60
aggagcacag aggaggggtg cagggagagt ccaggggggct acattcctcc tccagctatt    120
tatgtcttca ggcccaggtg cttcctacct atgggttctc caggttatcc ttgtgtcctc    180
tccttgtata aactccctct t                                               201
```

<210> SEQ ID NO 27
<211> LENGTH: 201
<212> TYPE: DNA
<213> ORGANISM: Homo sapiens

<400> SEQUENCE: 27

```
acaaggggga ggcaggcgca caccgcaatg ccaaagagac catgaccatc gagaacccaa      60
aactggagga cactgcaggg gacaccgggc acagcagcct cgaggcccccc cgcagccctg    120 acaccctggc cccggtggct tctgagcggc tgcccccaca gcagtcaggg gggcccagag    180
gttgagacaa aacgtaaaga c                                               201
```

<210> SEQ ID NO 28
<211> LENGTH: 201
<212> TYPE: DNA
<213> ORGANISM: Homo sapiens

<400> SEQUENCE: 28

```
acaaggggga ggcaggcgca caccgcaatg ccaaagagac catgaccatc gagaacccaa      60
aactggagga cactgcaggg gacaccgggc acagcagcct tgaggccccc cgcagccctg    120
acaccctggc cccggtggct tctgagcggc tgcccccaca gcagtcaggg gggcccagag    180
gttgagacaa aacgtaaaga c                                               201
```

<210> SEQ ID NO 29
<211> LENGTH: 201
<212> TYPE: DNA
<213> ORGANISM: Homo sapiens

<400> SEQUENCE: 29

```
ttggtctaaa gtatactttg gtatcaggat tgcaactcta gatttcgtgc tgtttccatt      60
tgcctttatt tttagccttt ttgaatcact gtgttttaag attagttcct gtattctgcg    120
tagagttagg ttttgcttta tatgccaatt cgacaatttt ttttctttta actaaaaagg    180
tgagttgagc tcattcacat t                                               201
```

<210> SEQ ID NO 30
<211> LENGTH: 201
<212> TYPE: DNA
<213> ORGANISM: Homo sapiens

```
<400> SEQUENCE: 30
ttggtctaaa gtatactttg gtatcaggat tgcaactcta gatttcgtgc tgtttccatt    60
tgcctttatt tttagccttt ttgaatcact gtgttttaag tttagttcct gtattctgcg   120
tagagttagg ttttgcttta tatgccaatt cgacaatttt ttttctttta actaaaaagg   180
tgagttgagc tcattcacat t                                             201

<210> SEQ ID NO 31
<211> LENGTH: 201
<212> TYPE: DNA
<213> ORGANISM: Homo sapiens

<400> SEQUENCE: 31
acctaggcag ttttatctgt gtgcaaaatt tagaaatgtc attcctgtgg aaatgagcaa    60
atcataaata catcacagaa aagaagtcgc tattttttg tctttaagtt gttttatagt    120
taaattgtgt cagagagttt gccatctatt ttattcctaa aaaggcctgg tggagaatat   180
atgactttcc ttgatgtaga g                                             201

<210> SEQ ID NO 32
<211> LENGTH: 201
<212> TYPE: DNA
<213> ORGANISM: Homo sapiens

<400> SEQUENCE: 32
acctaggcag ttttatctgt gtgcaaaatt tagaaatgtc attcctgtgg aaatgagcaa    60
atcataaata catcacagaa aagaagtcgc tattttttg actttaagtt gttttatagt    120
taaattgtgt cagagagttt gccatctatt ttattcctaa aaaggcctgg tggagaatat   180
atgactttcc ttgatgtaga g                                             201

<210> SEQ ID NO 33
<211> LENGTH: 201
<212> TYPE: DNA
<213> ORGANISM: Homo sapiens

<400> SEQUENCE: 33
tgcctgtgcc atgaagctcc gcaggggccc ttccaaccct gggaatgtgt tgccaacaag    60
atcccttctg tccctgtcag gcagaggtgg cagagcactc tttggcagta agctttgtac   120
ccgaaccatt tcttttttca cagtctttag ataaggcagt ttgagttcat ttcaatagct   180
ggtacttccc gggttctgcc a                                             201

<210> SEQ ID NO 34
<211> LENGTH: 201
<212> TYPE: DNA
<213> ORGANISM: Homo sapiens

<400> SEQUENCE: 34
tgcctgtgcc atgaagctcc gcaggggccc ttccaaccct gggaatgtgt tgccaacaag    60
atcccttctg tccctgtcag gcagaggtgg cagagcactc cttggcagta agctttgtac   120
ccgaaccatt tcttttttca cagtctttag ataaggcagt ttgagttcat ttcaatagct   180
ggtacttccc gggttctgcc a                                             201

<210> SEQ ID NO 35
<211> LENGTH: 201
<212> TYPE: DNA
<213> ORGANISM: Homo sapiens
```

<400> SEQUENCE: 35
agcgtagtag caaactgctg gcccacagcc tgctatgaag taggagttca ttaccttctt      60
cgctccaggt cttgacatgg tccaaagact tgtcttttga agcagccctg ttgtatcctc     120
ttgagttgtc atgacattgt ctgctggtct tccagtggca aaatatccta gactttcaga     180
gctgaaaaaa aaaggtactt t                                                201

<210> SEQ ID NO 36
<211> LENGTH: 201
<212> TYPE: DNA
<213> ORGANISM: Homo sapiens

<400> SEQUENCE: 36
agcgtagtag caaactgctg gcccacagcc tgctatgaag taggagttca ttaccttctt      60
cgctccaggt cttgacatgg tccaaagact tgtcttttga tgcagccctg ttgtatcctc     120
ttgagttgtc atgacattgt ctgctggtct tccagtggca aaatatccta gactttcaga     180
gctgaaaaaa aaaggtactt t                                                201

<210> SEQ ID NO 37
<211> LENGTH: 201
<212> TYPE: DNA
<213> ORGANISM: Homo sapiens

<400> SEQUENCE: 37
gatattgctg ataaagagtt aagtgaagga agtacttaca ggttactaag gactgaaggt      60
ggtgtttttc aaaaaaaatc tcaaaccaaa agcaaaatta ttaaagaagt aatatgctat     120
aatcccagaa gatggatgta gaagaagaa atctgagtgg aataaaggac cttctaccac     180
caatatcagt caatccaata a                                                201

<210> SEQ ID NO 38
<211> LENGTH: 201
<212> TYPE: DNA
<213> ORGANISM: Homo sapiens

<400> SEQUENCE: 38
gatattgctg ataaagagtt aagtgaagga agtacttaca ggttactaag gactgaaggt      60
ggtgtttttc aaaaaaaatc tcaaaccaaa agcaaaatta gtaaagaagt aatatgctat     120
aatcccagaa gatggatgta gaagaagaa atctgagtgg aataaaggac cttctaccac     180
caatatcagt caatccaata a                                                201

<210> SEQ ID NO 39
<211> LENGTH: 201
<212> TYPE: DNA
<213> ORGANISM: Homo sapiens

<400> SEQUENCE: 39
ttatgtaatc tactcctagg tagctgatac tatagtaaga tgtaattttt ttttgtcttt      60
gcaaaggtgt tcttgttgct gacaaggaac agcagaatag cgaacaagtt tgtggctaaa     120
cattattccc agattttaaa aaatgttcag tgtgcacaat tgttactacc agatctttgt     180
cagaataatc tttctgtcac t                                                201

<210> SEQ ID NO 40
<211> LENGTH: 201
<212> TYPE: DNA

<210> SEQ ID NO 40
<211> LENGTH: 201
<212> TYPE: DNA
<213> ORGANISM: Homo sapiens

<400> SEQUENCE: 40

```
ttatgtaatc tactcctagg tagctgatac tatagtaaga tgtaattttt ttttgtcttt        60
gcaaaggtgt tcttgttgct gacaaggaac agcagaatag tgaacaagtt tgtggctaaa       120
cattattccc agattttaaa aaatgttcag tgtgcacaat tgttactacc agatctttgt       180
cagaataatc tttctgtcac t                                                 201
```

<210> SEQ ID NO 41
<211> LENGTH: 201
<212> TYPE: DNA
<213> ORGANISM: Homo sapiens

<400> SEQUENCE: 41

```
gagaaacttc tttgcatttg tgagaaaata gtctattgaa ctgcttccaa tctatcaaga        60
tcttgctgta cttccttcat ttactctccc ctgcttttgg ctgaagaatt tttaggcaaa       120
tccaagactc ctgtcgtttc cccgttccat ctgcaggcat ctctgagtgt tgagggcatt       180
tcttgtagcc cagtgctgtt a                                                 201
```

<210> SEQ ID NO 42
<211> LENGTH: 201
<212> TYPE: DNA
<213> ORGANISM: Homo sapiens

<400> SEQUENCE: 42

```
gagaaacttc tttgcatttg tgagaaaata gtctattgaa ctgcttccaa tctatcaaga        60
tcttgctgta cttccttcat ttactctccc ctgcttttgg atgaagaatt tttaggcaaa       120
tccaagactc ctgtcgtttc cccgttccat ctgcaggcat ctctgagtgt tgagggcatt       180
tcttgtagcc cagtgctgtt a                                                 201
```

<210> SEQ ID NO 43
<211> LENGTH: 201
<212> TYPE: DNA
<213> ORGANISM: Homo sapiens

<400> SEQUENCE: 43

```
ggaagcctcc tctgcccttg cctctcttgg aactcgaggt ccaccctgac aaagccacac        60
tgggtcccag ccgcagtgtc tctcctggcc cagggagcac atacctggat cctcctcctt       120
caccgtaaag ttgtagctgg actgattgaa gatgggcagg ttatcattga tgtcctgcag       180
tcagagacag gtctgagtcc c                                                 201
```

<210> SEQ ID NO 44
<211> LENGTH: 201
<212> TYPE: DNA
<213> ORGANISM: Homo sapiens

<400> SEQUENCE: 44

```
ggaagcctcc tctgcccttg cctctcttgg aactcgaggt ccaccctgac aaagccacac        60
tgggtcccag ccgcagtgtc tctcctggcc cagggagcac gtacctggat cctcctcctt       120
caccgtaaag ttgtagctgg actgattgaa gatgggcagg ttatcattga tgtcctgcag       180
tcagagacag gtctgagtcc c                                                 201
```

<210> SEQ ID NO 45
<211> LENGTH: 201

```
<210> SEQ ID NO 45
<211> LENGTH: 201
<212> TYPE: DNA
<213> ORGANISM: Homo sapiens

<400> SEQUENCE: 45
aatcagttta agcccctcct tgttagatta ggttcttacg atatgcttag gttctgagtt      60
gttttatttc cctgtttgtt ttaccttaag ctttttttaca gttcattgct gcctggtttg    120
agttggttcc ttattccttc tccttcaagt tgagttacaa ctagtaattg cttgcctaac    180
tttacctgat aagattttat a                                               201

<210> SEQ ID NO 46
<211> LENGTH: 201
<212> TYPE: DNA
<213> ORGANISM: Homo sapiens

<400> SEQUENCE: 46
aatcagttta agcccctcct tgttagatta ggttcttacg atatgcttag gttctgagtt      60
gttttatttc cctgtttgtt ttaccttaag ctttttttaca attcattgct gcctggtttg    120
agttggttcc ttattccttc tccttcaagt tgagttacaa ctagtaattg cttgcctaac    180
tttacctgat aagattttat a                                               201

<210> SEQ ID NO 47
<211> LENGTH: 201
<212> TYPE: DNA
<213> ORGANISM: Homo sapiens

<400> SEQUENCE: 47
gcttgaggta gaaatggag cagggtaggg accaagtgga aataattgc catagctact        60
gagacaggag agaagaaaat gtgtatatga gaaaacagtt tgttttggct agaataaatg    120
atgcatgagg gcaaaaagcc agagtgtgct tataaaagta agtggtagct gaaactcatc    180
agaataatga caaaataaag g                                              201

<210> SEQ ID NO 48
<211> LENGTH: 201
<212> TYPE: DNA
<213> ORGANISM: Homo sapiens

<400> SEQUENCE: 48
gcttgaggta gaaatggag cagggtaggg accaagtgga aataattgc catagctact        60
gagacaggag agaagaaaat gtgtatatga gaaaacagtt cgttttggct agaataaatg    120
atgcatgagg gcaaaaagcc agagtgtgct tataaaagta agtggtagct gaaactcatc    180
agaataatga caaaataaag g                                              201

<210> SEQ ID NO 49
<211> LENGTH: 201
<212> TYPE: DNA
<213> ORGANISM: Homo sapiens

<400> SEQUENCE: 49
tctctgttga gtaacataac attttcatta accccttaaag gctatggagc cagaagcata     60
gcaagtaaac acccatgacc agccacttga ggtgaagaga ccagatttat ttagattttg    120
tagccatgtt gtatagttca ttcaggatct caagcttccg tacatacgat ttctcttaaa    180
tttaattctg aaaattaaaa t                                              201

<210> SEQ ID NO 50
```

<211> LENGTH: 201
<212> TYPE: DNA
<213> ORGANISM: Homo sapiens

<400> SEQUENCE: 50

```
tctctgttga gtaacataac attttcatta acccttaaag gctatggagc cagaagcata      60
gcaagtaaac acccatgacc agccacttga ggtgaagaga tcagatttat ttagattttg     120
tagccatgtt gtatagttca ttcaggatct caagcttccg tacatacgat ttctcttaaa     180
tttaattctg aaaattaaaa t                                                201
```

<210> SEQ ID NO 51
<211> LENGTH: 201
<212> TYPE: DNA
<213> ORGANISM: Homo sapiens

<400> SEQUENCE: 51

```
ggggcatgca tttgggaagc agctgtctgt cttcagtttg tgatagtaaa acccagtggt      60
gttatagctc atgctacctg gtagggtact gacatgggaa gagtgaagag agaagtgagt     120
cttggacctg gttcagacac tctctgggaa gaggaagaac acaaaggcca atgaaagaca     180
ggcaacgcgg gaagacgcat a                                                201
```

<210> SEQ ID NO 52
<211> LENGTH: 201
<212> TYPE: DNA
<213> ORGANISM: Homo sapiens

<400> SEQUENCE: 52

```
ggggcatgca tttgggaagc agctgtctgt cttcagtttg tgatagtaaa acccagtggt      60
gttatagctc atgctacctg gtagggtact gacatgggaa cagtgaagag agaagtgagt     120
cttggacctg gttcagacac tctctgggaa gaggaagaac acaaaggcca atgaaagaca     180
ggcaacgcgg gaagacgcat a                                                201
```

<210> SEQ ID NO 53
<211> LENGTH: 201
<212> TYPE: DNA
<213> ORGANISM: Homo sapiens

<400> SEQUENCE: 53

```
tcaacccaaa caggaaaaat ggcttttgga aaaactattc gaatttgatc tagaagatgt      60
tgttcaaggg aaacagcatg cagctcctag aaccaacaga cgaaaagatc aattcacttt     120
acattttgtc cactccatat ctagttaaaa aaaatctcaa ttctttttt aaaaaacaaa      180
ttttaatgtg catatttaat a                                                201
```

<210> SEQ ID NO 54
<211> LENGTH: 201
<212> TYPE: DNA
<213> ORGANISM: Homo sapiens

<400> SEQUENCE: 54

```
tcaacccaaa caggaaaaat ggcttttgga aaaactattc gaatttgatc tagaagatgt      60
tgttcaaggg aaacagcatg cagctcctag aaccaacaga tgaaaagatc aattcacttt     120
acattttgtc cactccatat ctagttaaaa aaaatctcaa ttctttttt aaaaaacaaa      180
ttttaatgtg catatttaat a                                                201
```

<210> SEQ ID NO 55
<211> LENGTH: 201
<212> TYPE: DNA
<213> ORGANISM: Homo sapiens

<400> SEQUENCE: 55

```
ctaatcttga catctctcct aggggaagaa tatcacaggc taatagcgtg gttgggggtg      60
aagatgatag cagttattaa atcaggaatc tcttttatgt gtgtccttgt tacattgagg     120
ttaagagaca aaatcattgg cagtgcaatc tctttccagg atttcgtttg ctgtggcatt     180
ggttatatca gagcacttta a                                              201
```

<210> SEQ ID NO 56
<211> LENGTH: 201
<212> TYPE: DNA
<213> ORGANISM: Homo sapiens

<400> SEQUENCE: 56

```
ctaatcttga catctctcct aggggaagaa tatcacaggc taatagcgtg gttgggggtg      60
aagatgatag cagttattaa atcaggaatc tcttttatgt atgtccttgt tacattgagg     120
ttaagagaca aaatcattgg cagtgcaatc tctttccagg atttcgtttg ctgtggcatt     180
ggttatatca gagcacttta a                                              201
```

<210> SEQ ID NO 57
<211> LENGTH: 201
<212> TYPE: DNA
<213> ORGANISM: Homo sapiens

<400> SEQUENCE: 57

```
taactaatat cataagtgac agcaaaataa actacaaact attgcataac tatctcaata      60
ttttaccaaa tatatgcctc ttatccaaca tgagaatcca atcttttatt taactatata     120
ctgaaaatgt cttttaagcc attcttcacc aaactaattt gtaaattatc ccataaaatt     180
ccttcctacc tttcaaagct t                                              201
```

<210> SEQ ID NO 58
<211> LENGTH: 201
<212> TYPE: DNA
<213> ORGANISM: Homo sapiens

<400> SEQUENCE: 58

```
taactaatat cataagtgac agcaaaataa actacaaact attgcataac tatctcaata      60
ttttaccaaa tatatgcctc ttatccaaca tgagaatcca gtcttttatt taactatata     120
ctgaaaatgt cttttaagcc attcttcacc aaactaattt gtaaattatc ccataaaatt     180
ccttcctacc tttcaaagct t                                              201
```

<210> SEQ ID NO 59
<211> LENGTH: 201
<212> TYPE: DNA
<213> ORGANISM: Homo sapiens

<400> SEQUENCE: 59

```
agcgtatact tgggggcagt gagtgggcct caaagaagtg gcaaaggcag ggccctcagg      60
ctggggtgtt gaggaagtcc tagatgacaa tcgtataata tattcatata aagacagagc     120
aatagcaaca tgtcctcagc cttacaaaag gaacttaaac gtgaaatttt cttccaaatt     180
atgtggtggc aaggtcagta a                                              201
```

<210> SEQ ID NO 60
<211> LENGTH: 201
<212> TYPE: DNA
<213> ORGANISM: Homo sapiens

<400> SEQUENCE: 60

```
agcgtatact tgggggcagt gagtgggcct caaagaagtg gcaaaggcag ggccctcagg      60
ctggggtgtt gaggaagtcc tagatgacaa tcgtataata cattcatata aagacagagc     120
aatagcaaca tgtcctcagc cttacaaaag gaacttaaac gtgaaatttt cttccaaatt     180
atgtggtggc aaggtcagta a                                               201
```

<210> SEQ ID NO 61
<211> LENGTH: 201
<212> TYPE: DNA
<213> ORGANISM: Homo sapiens

<400> SEQUENCE: 61

```
aggcaggctc tgaactcagg cacccccaga gctggatcct gttcgctcct cttaatggtc      60
atgcgtggga tcttatttaa cctctttaag ccctggcttc tcatctgcaa attggcaatg     120
ataatggtgc aagcctcatg gagctgtgag aattaaatga agcatatgtg tgtaaaagca     180
gttggcacag tacttggcat a                                               201
```

<210> SEQ ID NO 62
<211> LENGTH: 201
<212> TYPE: DNA
<213> ORGANISM: Homo sapiens

<400> SEQUENCE: 62

```
aggcaggctc tgaactcagg cacccccaga gctggatcct gttcgctcct cttaatggtc      60
atgcgtggga tcttatttaa cctctttaag ccctggcttc ccatctgcaa attggcaatg     120
ataatggtgc aagcctcatg gagctgtgag aattaaatga agcatatgtg tgtaaaagca     180
gttggcacag tacttggcat a                                               201
```

<210> SEQ ID NO 63
<211> LENGTH: 201
<212> TYPE: DNA
<213> ORGANISM: Homo sapiens

<400> SEQUENCE: 63

```
tataacataa atgagaaaaa ataacctatc aataataaca atgaagatga ataggcttaa      60
cttatctatt ttgtctcata aagcacaacc aactacatgc actaaagtag agccacattt     120
agaaccaagt gactcagaaa aactaaaaat aagagataga gaaggtttac caggcaaatg     180
gaaacaataa gaatgcagag a                                               201
```

<210> SEQ ID NO 64
<211> LENGTH: 201
<212> TYPE: DNA
<213> ORGANISM: Homo sapiens

<400> SEQUENCE: 64

```
tataacataa atgagaaaaa ataacctatc aataataaca atgaagatga ataggcttaa      60
cttatctatt ttgtctcata aagcacaacc aactacatgc cctaaagtag agccacattt     120
agaaccaagt gactcagaaa aactaaaaat aagagataga gaaggtttac caggcaaatg     180
gaaacaataa gaatgcagag a                                               201
```

<210> SEQ ID NO 65
<211> LENGTH: 201
<212> TYPE: DNA
<213> ORGANISM: Homo sapiens

<400> SEQUENCE: 65

```
ttcttctttc ctttcaaagg catttactta aaccagactt ttccctcatc tctctcgatc      60
actttggaga ctcaagctaa catactaact cttgctttca tacacactttt ctgtttcttc    120
ttcctgtagt taataacatc ggatggagtg tgttgtaata aatacaattg agggccagga    180
gcaatggctc actcctgtaa t                                                201
```

<210> SEQ ID NO 66
<211> LENGTH: 201
<212> TYPE: DNA
<213> ORGANISM: Homo sapiens

<400> SEQUENCE: 66

```
ttcttctttc ctttcaaagg catttactta aaccagactt ttccctcatc tctctcgatc      60
actttggaga ctcaagctaa catactaact cttgctttca cacacactttt ctgtttcttc    120
ttcctgtagt taataacatc ggatggagtg tgttgtaata aatacaattg agggccagga    180
gcaatggctc actcctgtaa t                                                201
```

<210> SEQ ID NO 67
<211> LENGTH: 201
<212> TYPE: DNA
<213> ORGANISM: Homo sapiens

<400> SEQUENCE: 67

```
acacggcagc gtagtgaagt gctgaacggt gctagcagct agttaaatag ttctcccctt      60
agattgaccc ttagatctat ttacctataa ctgaaatcca ttggttttac ttctgttctc    120
tgtagcaaca aagcgcaaaa atcactttct ctgacaaggt ctcatgctgt tcagtcattt    180
gctattttt  ctaactcttc t                                                201
```

<210> SEQ ID NO 68
<211> LENGTH: 201
<212> TYPE: DNA
<213> ORGANISM: Homo sapiens

<400> SEQUENCE: 68

```
acacggcagc gtagtgaagt gctgaacggt gctagcagct agttaaatag ttctcccctt      60
agattgaccc ttagatctat ttacctataa ctgaaatcca ctggttttac ttctgttctc    120
tgtagcaaca aagcgcaaaa atcactttct ctgacaaggt ctcatgctgt tcagtcattt    180
gctattttt  ctaactcttc t                                                201
```

<210> SEQ ID NO 69
<211> LENGTH: 201
<212> TYPE: DNA
<213> ORGANISM: Homo sapiens

<400> SEQUENCE: 69

```
gcagaaaaac agaacatcag ctgttaacct taaaaatcag ggaaatcaca agctaacaaa      60
aaagagaaaa tggtaactct catagccaag gtagctatgg aaacagcttc ccctggaatg    120
gtttcaagta gcctctgcta acaacagtca tcatgagagc tctggtagcc agtgctagag    180
```

| | |
|---|---|
| acaggcagaa caaaacaatc t | 201 |

<210> SEQ ID NO 70
<211> LENGTH: 201
<212> TYPE: DNA
<213> ORGANISM: Homo sapiens

<400> SEQUENCE: 70

| | |
|---|---|
| gcagaaaaac agaacatcag ctgttaacct taaaaatcag ggaaatcaca agctaacaaa | 60 |
| aaagagaaaa tggtaactct catagccaag gtagctatgg gaacagcttc ccctggaatg | 120 |
| gtttcaagta gcctctgcta acaacagtca tcatgagagc tctggtagcc agtgctagag | 180 |
| acaggcagaa caaaacaatc t | 201 |

<210> SEQ ID NO 71
<211> LENGTH: 201
<212> TYPE: DNA
<213> ORGANISM: Homo sapiens

<400> SEQUENCE: 71

| | |
|---|---|
| atttcatatt tcaataactg gaatgttcag ctgaaggaca gtcttcagac actgatcagg | 60 |
| tattgtctcc atttctccgt gactgtttca gctctgcccc cttcagctt catccccacg | 120 |
| tgggttttcc tcatcttgtg gggtagtttc cagggacaac agggatccat gcttctgccc | 180 |
| aagcaaatgc cactcttcta g | 201 |

<210> SEQ ID NO 72
<211> LENGTH: 201
<212> TYPE: DNA
<213> ORGANISM: Homo sapiens

<400> SEQUENCE: 72

| | |
|---|---|
| atttcatatt tcaataactg gaatgttcag ctgaaggaca gtcttcagac actgatcagg | 60 |
| tattgtctcc atttctccgt gactgtttca gctctgcccc cttcagctt catccccacg | 120 |
| tgggttttcc tcatcttgtg gggtagtttc cagggacaac agggatccat gcttctgccc | 180 |
| aagcaaatgc cactcttcta g | 201 |

<210> SEQ ID NO 73
<211> LENGTH: 201
<212> TYPE: DNA
<213> ORGANISM: Homo sapiens

<400> SEQUENCE: 73

| | |
|---|---|
| gttctctgag cttaggttgt tctcattcta tttctctcaa aagcagctca aagcattacc | 60 |
| ctgaagtcta aataagatga aaacattctc aaaatatcta agctcttcta ggctaaaagg | 120 |
| aagaaattta atttctctcc tcgggagacc aatctgtaag tgcacaaact aattaaccac | 180 |
| tacctgctga agagggagac c | 201 |

<210> SEQ ID NO 74
<211> LENGTH: 201
<212> TYPE: DNA
<213> ORGANISM: Homo sapiens

<400> SEQUENCE: 74

| | |
|---|---|
| gttctctgag cttaggttgt tctcattcta tttctctcaa aagcagctca aagcattacc | 60 |
| ctgaagtcta aataagatga aaacattctc aaaatatcta agctcttcta ggctaaaagg | 120 |
| aagaaattta atttctctcc tcgggagacc aatctgtaag tgcacaaact aattaaccac | 180 | tacctgctga agagggagac c    201

<210> SEQ ID NO 75
<211> LENGTH: 201
<212> TYPE: DNA
<213> ORGANISM: Homo sapiens

<400> SEQUENCE: 75
agaactgtat tgtagccctg ccattgtttc ccagtctggg aagacttaa gcagaaacta    60 ggacttaatt ctgacatttt agttatttct ctgtaggggg aaggttccag attgagcatc    120
tgggcattgg gaaaaatctg gttagaaatt tgggccttcc tgcagattgc gttctctgca    180
gccttatggt accagtcagt t    201

<210> SEQ ID NO 76
<211> LENGTH: 201
<212> TYPE: DNA
<213> ORGANISM: Homo sapiens

<400> SEQUENCE: 76
agaactgtat tgtagccctg ccattgtttc ccagtctggg aagacttaa gcagaaacta    60 ggacttaatt ctgacatttt agttatttct ctgtaggggg gaggttccag attgagcatc    120
tgggcattgg gaaaaatctg gttagaaatt tgggccttcc tgcagattgc gttctctgca    180
gccttatggt accagtcagt t    201

<210> SEQ ID NO 77
<211> LENGTH: 201
<212> TYPE: DNA
<213> ORGANISM: Homo sapiens

<400> SEQUENCE: 77
cagcattgat tgactcccgt gagcaaagaa gccattagca ctctcacact tcttccctcc    60
aaacctcccg ccacctccca gttttcgtta gctagagcat aattttactc tgtcaggact    120
gtagtatttg cattctgctt tgtagcaata attctcaaca attttttagt attaagtcta    180
tatttaaatg gattcaatgt t    201

<210> SEQ ID NO 78
<211> LENGTH: 201
<212> TYPE: DNA
<213> ORGANISM: Homo sapiens

<400> SEQUENCE: 78
cagcattgat tgactcccgt gagcaaagaa gccattagca ctctcacact tcttccctcc    60
aaacctcccg ccacctccca gttttcgtta gctagagcat cattttactc tgtcaggact    120
gtagtatttg cattctgctt tgtagcaata attctcaaca attttttagt attaagtcta    180
tatttaaatg gattcaatgt t    201

<210> SEQ ID NO 79
<211> LENGTH: 201
<212> TYPE: DNA
<213> ORGANISM: Homo sapiens

<400> SEQUENCE: 79
atggttttta actcttttct gaaaacattt tcagatgaca ttcctgaaag ctcactcttc    60
tcaccaatgc catcagagga aaaggctgct tcccctccca aacctctgct ttcaaatgcc    120

```
tcggcaactc cagttggcag aaggggccgt ctggccaatc ttgctgcaac tatttgctcc      180
tgggaagatg atgtaaatca c                                               201
```

<210> SEQ ID NO 80
<211> LENGTH: 201
<212> TYPE: DNA
<213> ORGANISM: Homo sapiens

<400> SEQUENCE: 80

```
atggttttta actctttttct gaaaacattt tcagatgaca ttcctgaaag ctcactcttc      60
tcaccaatgc catcagagga aaaggctgct tcccctccca gacctctgct ttcaaatgcc     120
tcggcaactc cagttggcag aaggggccgt ctggccaatc ttgctgcaac tatttgctcc     180
tgggaagatg atgtaaatca c                                              201
```

<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81

```
acgttggatg atacaactta aaggccaagg                                      30
```

<210> SEQ ID NO 82
<211> LENGTH: 30
<212> TYPE: DNA
<213> ORGANISM: Artificial Sequence
<220> FEATURE:
<223> OTHER INFORMATION: primer

<400> SEQUENCE: 82

```
acgttggatg gcccatattc aagctgattg                                      30
```

<210> SEQ ID NO 83
<211> LENGTH: 20
<212> TYPE: DNA
<213> ORGANISM: Artificial Sequence
<220> FEATURE:
<223> OTHER INFORMATION: primer

<400> SEQUENCE: 83

```
ttaaaggcca aggagcccaa                                                 20
```

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84

```
acgttggatg gtaatctcct ttgtcctctc                                      30
```

<210> SEQ ID NO 85
<211> LENGTH: 31
<212> TYPE: DNA
<213> ORGANISM: Artificial Sequence
<220> FEATURE:
<223> OTHER INFORMATION: primer

<400> SEQUENCE: 85

```
acgttggatg caaatggaaa ttttaggacg g                                    31
```

```
<210> SEQ ID NO 86
<211> LENGTH: 21
<212> TYPE: DNA
<213> ORGANISM: Artificial Sequence
<220> FEATURE:
<223> OTHER INFORMATION: primer

<400> SEQUENCE: 86
ttgtcctctc aaagacattt a                                           21

<210> SEQ ID NO 87
<211> LENGTH: 30
<212> TYPE: DNA
<213> ORGANISM: Artificial Sequence
<220> FEATURE:
<223> OTHER INFORMATION: primer

<400> SEQUENCE: 87
acgttggatg ctcaatagga aggagtcctg                                  30

<210> SEQ ID NO 88
<211> LENGTH: 30
<212> TYPE: DNA
<213> ORGANISM: Artificial Sequence
<220> FEATURE:
<223> OTHER INFORMATION: primer

<400> SEQUENCE: 88
acgttggatg aaacatctgt gggtgacagg                                  30

<210> SEQ ID NO 89
<211> LENGTH: 17
<212> TYPE: DNA
<213> ORGANISM: Artificial Sequence
<220> FEATURE:
<223> OTHER INFORMATION: primer

<400> SEQUENCE: 89
ctgagagcct ctgtcac                                                17

<210> SEQ ID NO 90
<211> LENGTH: 30
<212> TYPE: DNA
<213> ORGANISM: Artificial Sequence
<220> FEATURE:
<223> OTHER INFORMATION: primer

<400> SEQUENCE: 90
acgttggatg catgtcaaac taacatgtcc                                  30

<210> SEQ ID NO 91
<211> LENGTH: 30
<212> TYPE: DNA
<213> ORGANISM: Artificial Sequence
<220> FEATURE:
<223> OTHER INFORMATION: primer

<400> SEQUENCE: 91
acgttggatg gggagaagta caagtcaaag                                  30

<210> SEQ ID NO 92
<211> LENGTH: 23
<212> TYPE: DNA
<213> ORGANISM: Artificial Sequence
<220> FEATURE:
```

<223> OTHER INFORMATION: primer

<400> SEQUENCE: 92
ttcttgatca attttaacac ctc                                          23

<210> SEQ ID NO 93
<211> LENGTH: 30
<212> TYPE: DNA
<213> ORGANISM: Artificial Sequence
<220> FEATURE:
<223> OTHER INFORMATION: primer

<400> SEQUENCE: 93
acgttggatg cataggtaac tttgagaagg                                   30

<210> SEQ ID NO 94
<211> LENGTH: 30
<212> TYPE: DNA
<213> ORGANISM: Artificial Sequence
<220> FEATURE:
<223> OTHER INFORMATION: primer

<400> SEQUENCE: 94
acgttggatg aggtacctga atccttgtag                                   30

<210> SEQ ID NO 95
<211> LENGTH: 23
<212> TYPE: DNA
<213> ORGANISM: Artificial Sequence
<220> FEATURE:
<223> OTHER INFORMATION: primer

<400> SEQUENCE: 95
gagaaggaac tatgataatc atg                                          23

<210> SEQ ID NO 96
<211> LENGTH: 30
<212> TYPE: DNA
<213> ORGANISM: Artificial Sequence
<220> FEATURE:
<223> OTHER INFORMATION: primer

<400> SEQUENCE: 96
acgttggatg agcagtcttg acaagatgtg                                   30

<210> SEQ ID NO 97
<211> LENGTH: 30
<212> TYPE: DNA
<213> ORGANISM: Artificial Sequence
<220> FEATURE:
<223> OTHER INFORMATION: primer

<400> SEQUENCE: 97
acgttggatg tgtgtctgaa ggaaccacag                                   30

<210> SEQ ID NO 98
<211> LENGTH: 19
<212> TYPE: DNA
<213> ORGANISM: Artificial Sequence
<220> FEATURE:
<223> OTHER INFORMATION: primer

<400> SEQUENCE: 98
ctgcctctag gccccctga                                               19

```
<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
acgttggatg agccaataag aaacctcagg                                      30

<210> SEQ ID NO 100
<211> LENGTH: 30
<212> TYPE: DNA
<213> ORGANISM: Artificial Sequence
<220> FEATURE:
<223> OTHER INFORMATION: primer

<400> SEQUENCE: 100
acgttggatg agtgacttga gtaactgtgg                                      30

<210> SEQ ID NO 101
<211> LENGTH: 20
<212> TYPE: DNA
<213> ORGANISM: Artificial Sequence
<220> FEATURE:
<223> OTHER INFORMATION: primer

<400> SEQUENCE: 101
aaacctcagg agaggatcca                                                 20

<210> SEQ ID NO 102
<211> LENGTH: 30
<212> TYPE: DNA
<213> ORGANISM: Artificial Sequence
<220> FEATURE:
<223> OTHER INFORMATION: primer

<400> SEQUENCE: 102
acgttggatg tggaggtgat gccttagttg                                      30

<210> SEQ ID NO 103
<211> LENGTH: 30
<212> TYPE: DNA
<213> ORGANISM: Artificial Sequence
<220> FEATURE:
<223> OTHER INFORMATION: primer

<400> SEQUENCE: 103
acgttggatg tgccctgtag tcttcctgtc                                      30

<210> SEQ ID NO 104
<211> LENGTH: 22
<212> TYPE: DNA
<213> ORGANISM: Artificial Sequence
<220> FEATURE:
<223> OTHER INFORMATION: primer

<400> SEQUENCE: 104
agggaacatt tcaggtataa ag                                              22

<210> SEQ ID NO 105
<211> LENGTH: 31
<212> TYPE: DNA
<213> ORGANISM: Artificial Sequence
<220> FEATURE:
<223> OTHER INFORMATION: primer
```

<400> SEQUENCE: 105
acgttggatg gatgaaaatg taatatccat g                                  31

<210> SEQ ID NO 106
<211> LENGTH: 30
<212> TYPE: DNA
<213> ORGANISM: Artificial Sequence
<220> FEATURE:
<223> OTHER INFORMATION: primer

<400> SEQUENCE: 106
acgttggatg caaaattccg tttctttcag                                    30

<210> SEQ ID NO 107
<211> LENGTH: 24
<212> TYPE: DNA
<213> ORGANISM: Artificial Sequence
<220> FEATURE:
<223> OTHER INFORMATION: primer

<400> SEQUENCE: 107
taatatccat gaagaataag acaa                                          24

<210> SEQ ID NO 108
<211> LENGTH: 30
<212> TYPE: DNA
<213> ORGANISM: Artificial Sequence
<220> FEATURE:
<223> OTHER INFORMATION: primer

<400> SEQUENCE: 108
acgttggatg tgattccaag ggacaggttc                                    30

<210> SEQ ID NO 109
<211> LENGTH: 30
<212> TYPE: DNA
<213> ORGANISM: Artificial Sequence
<220> FEATURE:
<223> OTHER INFORMATION: primer

<400> SEQUENCE: 109
acgttggatg cctacctggt ttctcttctc                                    30

<210> SEQ ID NO 110
<211> LENGTH: 20
<212> TYPE: DNA
<213> ORGANISM: Artificial Sequence
<220> FEATURE:
<223> OTHER INFORMATION: primer

<400> SEQUENCE: 110
gttccaggag cagacatatc                                               20

<210> SEQ ID NO 111
<211> LENGTH: 30
<212> TYPE: DNA
<213> ORGANISM: Artificial Sequence
<220> FEATURE:
<223> OTHER INFORMATION: primer

<400> SEQUENCE: 111
acgttggatg agaagcccac cactgagatg                                    30

<210> SEQ ID NO 112
<211> LENGTH: 30

```
<212> TYPE: DNA
<213> ORGANISM: Artificial Sequence
<220> FEATURE:
<223> OTHER INFORMATION: primer

<400> SEQUENCE: 112
acgttggatg aaaatccaaa ctccaccccc                                    30

<210> SEQ ID NO 113
<211> LENGTH: 19
<212> TYPE: DNA
<213> ORGANISM: Artificial Sequence
<220> FEATURE:
<223> OTHER INFORMATION: primer

<400> SEQUENCE: 113
gggcacagag aaccctcaa                                                19

<210> SEQ ID NO 114
<211> LENGTH: 30
<212> TYPE: DNA
<213> ORGANISM: Artificial Sequence
<220> FEATURE:
<223> OTHER INFORMATION: primer

<400> SEQUENCE: 114
acgttggatg actgcaccat agaaccatcc                                    30

<210> SEQ ID NO 115
<211> LENGTH: 30
<212> TYPE: DNA
<213> ORGANISM: Artificial Sequence
<220> FEATURE:
<223> OTHER INFORMATION: primer

<400> SEQUENCE: 115
acgttggatg caaggaagga gtcaagacag                                    30

<210> SEQ ID NO 116
<211> LENGTH: 19
<212> TYPE: DNA
<213> ORGANISM: Artificial Sequence
<220> FEATURE:
<223> OTHER INFORMATION: primer

<400> SEQUENCE: 116
catagaacca tcctgcccc                                                19

<210> SEQ ID NO 117
<211> LENGTH: 30
<212> TYPE: DNA
<213> ORGANISM: Artificial Sequence
<220> FEATURE:
<223> OTHER INFORMATION: primer

<400> SEQUENCE: 117
acgttggatg ggcctgaaga cataaatagc                                    30

<210> SEQ ID NO 118
<211> LENGTH: 30
<212> TYPE: DNA
<213> ORGANISM: Artificial Sequence
<220> FEATURE:
<223> OTHER INFORMATION: primer

<400> SEQUENCE: 118
```

-continued acgttggatg aaattaggac ggacagagag    30

<210> SEQ ID NO 119
<211> LENGTH: 21
<212> TYPE: DNA
<213> ORGANISM: Artificial Sequence
<220> FEATURE:
<223> OTHER INFORMATION: primer

<400> SEQUENCE: 119
taaatagctg gaggaggaat g    21

<210> SEQ ID NO 120
<211> LENGTH: 30
<212> TYPE: DNA
<213> ORGANISM: Artificial Sequence
<220> FEATURE:
<223> OTHER INFORMATION: primer

<400> SEQUENCE: 120
acgttggatg aacccaaaac tggaggacac    30

<210> SEQ ID NO 121
<211> LENGTH: 29
<212> TYPE: DNA
<213> ORGANISM: Artificial Sequence
<220> FEATURE:
<223> OTHER INFORMATION: primer

<400> SEQUENCE: 121
acgttggatg agccgctcag aagccaccg    29

<210> SEQ ID NO 122
<211> LENGTH: 17
<212> TYPE: DNA
<213> ORGANISM: Artificial Sequence
<220> FEATURE:
<223> OTHER INFORMATION: primer

<400> SEQUENCE: 122
accgggcaca gcagcct    17

<210> SEQ ID NO 123
<211> LENGTH: 30
<212> TYPE: DNA
<213> ORGANISM: Artificial Sequence
<220> FEATURE:
<223> OTHER INFORMATION: primer

<400> SEQUENCE: 123
acgttggatg aactctacgc agaatacagg    30

<210> SEQ ID NO 124
<211> LENGTH: 30
<212> TYPE: DNA
<213> ORGANISM: Artificial Sequence
<220> FEATURE:
<223> OTHER INFORMATION: primer

<400> SEQUENCE: 124
acgttggatg ttcgtgctgt ttccatttgc    30

<210> SEQ ID NO 125
<211> LENGTH: 22
<212> TYPE: DNA
<213> ORGANISM: Artificial Sequence

```
<220> FEATURE:
<223> OTHER INFORMATION: primer

<400> SEQUENCE: 125
ctacgcagaa tacaggaact aa                                              22

<210> SEQ ID NO 126
<211> LENGTH: 30
<212> TYPE: DNA
<213> ORGANISM: Artificial Sequence
<220> FEATURE:
<223> OTHER INFORMATION: primer

<400> SEQUENCE: 126
acgttggatg catcacagaa aagaagtcgc                                      30

<210> SEQ ID NO 127
<211> LENGTH: 30
<212> TYPE: DNA
<213> ORGANISM: Artificial Sequence
<220> FEATURE:
<223> OTHER INFORMATION: primer

<400> SEQUENCE: 127
acgttggatg tagatggcaa actctctgac                                      30

<210> SEQ ID NO 128
<211> LENGTH: 23
<212> TYPE: DNA
<213> ORGANISM: Artificial Sequence
<220> FEATURE:
<223> OTHER INFORMATION: primer

<400> SEQUENCE: 128
gaaaagaagt cgctattttt ttg                                             23

<210> SEQ ID NO 129
<211> LENGTH: 30
<212> TYPE: DNA
<213> ORGANISM: Artificial Sequence
<220> FEATURE:
<223> OTHER INFORMATION: primer

<400> SEQUENCE: 129
acgttggatg ggttcgggta caaagcttac                                      30

<210> SEQ ID NO 130
<211> LENGTH: 30
<212> TYPE: DNA
<213> ORGANISM: Artificial Sequence
<220> FEATURE:
<223> OTHER INFORMATION: primer

<400> SEQUENCE: 130
acgttggatg atgtgttgcc aacaagatcc                                      30

<210> SEQ ID NO 131
<211> LENGTH: 21
<212> TYPE: DNA
<213> ORGANISM: Artificial Sequence
<220> FEATURE:
<223> OTHER INFORMATION: primer

<400> SEQUENCE: 131
gggtacaaag cttactgcca a                                               21
```

<210> SEQ ID NO 132
<211> LENGTH: 30
<212> TYPE: DNA
<213> ORGANISM: Artificial Sequence
<220> FEATURE:
<223> OTHER INFORMATION: primer

<400> SEQUENCE: 132
acgttggatg gaccagcaga caatgtcatg                                    30

<210> SEQ ID NO 133
<211> LENGTH: 30
<212> TYPE: DNA
<213> ORGANISM: Artificial Sequence
<220> FEATURE:
<223> OTHER INFORMATION: primer

<400> SEQUENCE: 133
acgttggatg ggtcttgaca tggtccaaag                                    30

<210> SEQ ID NO 134
<211> LENGTH: 19
<212> TYPE: DNA
<213> ORGANISM: Artificial Sequence
<220> FEATURE:
<223> OTHER INFORMATION: primer

<400> SEQUENCE: 134
gaggatacaa cagggctgc                                                19

<210> SEQ ID NO 135
<211> LENGTH: 30
<212> TYPE: DNA
<213> ORGANISM: Artificial Sequence
<220> FEATURE:
<223> OTHER INFORMATION: primer

<400> SEQUENCE: 135
acgttggatg gactgaaggt ggtgtttttc                                    30

<210> SEQ ID NO 136
<211> LENGTH: 30
<212> TYPE: DNA
<213> ORGANISM: Artificial Sequence
<220> FEATURE:
<223> OTHER INFORMATION: primer

<400> SEQUENCE: 136
acgttggatg ccatcttctg ggattatagc                                    30

<210> SEQ ID NO 137
<211> LENGTH: 24
<212> TYPE: DNA
<213> ORGANISM: Artificial Sequence
<220> FEATURE:
<223> OTHER INFORMATION: primer

<400> SEQUENCE: 137
aatctcaaac caaaagcaaa atta                                          24

<210> SEQ ID NO 138
<211> LENGTH: 29
<212> TYPE: DNA
<213> ORGANISM: Artificial Sequence
<220> FEATURE:
<223> OTHER INFORMATION: primer

<400> SEQUENCE: 138
acgttggatg tgttgctgac aaggaacag                                                29

<210> SEQ ID NO 139
<211> LENGTH: 31
<212> TYPE: DNA
<213> ORGANISM: Artificial Sequence
<220> FEATURE:
<223> OTHER INFORMATION: primer

<400> SEQUENCE: 139
acgttggatg ctgggaataa tgtttagcca c                                             31

<210> SEQ ID NO 140
<211> LENGTH: 21
<212> TYPE: DNA
<213> ORGANISM: Artificial Sequence
<220> FEATURE:
<223> OTHER INFORMATION: primer

<400> SEQUENCE: 140
tgacaaggaa cagcagaata g                                                        21

<210> SEQ ID NO 141
<211> LENGTH: 30
<212> TYPE: DNA
<213> ORGANISM: Artificial Sequence
<220> FEATURE:
<223> OTHER INFORMATION: primer

<400> SEQUENCE: 141
acgttggatg ccttcattta ctctcccctg                                               30

<210> SEQ ID NO 142
<211> LENGTH: 30
<212> TYPE: DNA
<213> ORGANISM: Artificial Sequence
<220> FEATURE:
<223> OTHER INFORMATION: primer

<400> SEQUENCE: 142
acgttggatg cgacaggagt cttggatttg                                               30

<210> SEQ ID NO 143
<211> LENGTH: 20
<212> TYPE: DNA
<213> ORGANISM: Artificial Sequence
<220> FEATURE:
<223> OTHER INFORMATION: primer

<400> SEQUENCE: 143
ttactctccc ctgcttttgg                                                          20

<210> SEQ ID NO 144
<211> LENGTH: 29
<212> TYPE: DNA
<213> ORGANISM: Artificial Sequence
<220> FEATURE:
<223> OTHER INFORMATION: primer

<400> SEQUENCE: 144
acgttggatg tgacaaagcc acactgggt                                                29

<210> SEQ ID NO 145

```
<211> LENGTH: 30
<212> TYPE: DNA
<213> ORGANISM: Artificial Sequence
<220> FEATURE:
<223> OTHER INFORMATION: primer

<400> SEQUENCE: 145
acgttggatg tacggtgaag gaggaggatc                                          30

<210> SEQ ID NO 146
<211> LENGTH: 18
<212> TYPE: DNA
<213> ORGANISM: Artificial Sequence
<220> FEATURE:
<223> OTHER INFORMATION: primer

<400> SEQUENCE: 146
tcctggccca gggagcac                                                      18

<210> SEQ ID NO 147
<211> LENGTH: 30
<212> TYPE: DNA
<213> ORGANISM: Artificial Sequence
<220> FEATURE:
<223> OTHER INFORMATION: primer

<400> SEQUENCE: 147
acgttggatg aaggaaccaa ctcaaaccag                                          30

<210> SEQ ID NO 148
<211> LENGTH: 30
<212> TYPE: DNA
<213> ORGANISM: Artificial Sequence
<220> FEATURE:
<223> OTHER INFORMATION: primer

<400> SEQUENCE: 148
acgttggatg cgatatgctt aggttctgag                                          30

<210> SEQ ID NO 149
<211> LENGTH: 21
<212> TYPE: DNA
<213> ORGANISM: Artificial Sequence
<220> FEATURE:
<223> OTHER INFORMATION: primer

<400> SEQUENCE: 149
ctcaaaccag gcagcaatga a                                                   21

<210> SEQ ID NO 150
<211> LENGTH: 30
<212> TYPE: DNA
<213> ORGANISM: Artificial Sequence
<220> FEATURE:
<223> OTHER INFORMATION: primer

<400> SEQUENCE: 150
acgttggatg gcttttttgcc ctcatgcatc                                         30

<210> SEQ ID NO 151
<211> LENGTH: 30
<212> TYPE: DNA
<213> ORGANISM: Artificial Sequence
<220> FEATURE:
<223> OTHER INFORMATION: primer

<400> SEQUENCE: 151
```
acgttggatg ctactgagac aggagagaag          30

<210> SEQ ID NO 152
<211> LENGTH: 23
<212> TYPE: DNA
<213> ORGANISM: Artificial Sequence
<220> FEATURE:
<223> OTHER INFORMATION: primer

<400> SEQUENCE: 152
gcatcattta ttctagccaa aac          23

<210> SEQ ID NO 153
<211> LENGTH: 30
<212> TYPE: DNA
<213> ORGANISM: Artificial Sequence
<220> FEATURE:
<223> OTHER INFORMATION: primer

<400> SEQUENCE: 153
acgttggatg aagtaaacac ccatgaccag          30

<210> SEQ ID NO 154
<211> LENGTH: 30
<212> TYPE: DNA
<213> ORGANISM: Artificial Sequence
<220> FEATURE:
<223> OTHER INFORMATION: primer

<400> SEQUENCE: 154
acgttggatg gcttgagatc ctgaatgaac          30

<210> SEQ ID NO 155
<211> LENGTH: 20
<212> TYPE: DNA
<213> ORGANISM: Artificial Sequence
<220> FEATURE:
<223> OTHER INFORMATION: primer

<400> SEQUENCE: 155
agccacttga ggtgaagaga          20

<210> SEQ ID NO 156
<211> LENGTH: 30
<212> TYPE: DNA
<213> ORGANISM: Artificial Sequence
<220> FEATURE:
<223> OTHER INFORMATION: primer

<400> SEQUENCE: 156
acgttggatg gtccaagact cacttctctc          30

<210> SEQ ID NO 157
<211> LENGTH: 30
<212> TYPE: DNA
<213> ORGANISM: Artificial Sequence
<220> FEATURE:
<223> OTHER INFORMATION: primer

<400> SEQUENCE: 157
acgttggatg acccagtggt gttatagctc          30

<210> SEQ ID NO 158
<211> LENGTH: 21
<212> TYPE: DNA

-continued

<213> ORGANISM: Artificial Sequence
<220> FEATURE:
<223> OTHER INFORMATION: primer

<400> SEQUENCE: 158
agactcactt ctctcttcac t                                            21

<210> SEQ ID NO 159
<211> LENGTH: 30
<212> TYPE: DNA
<213> ORGANISM: Artificial Sequence
<220> FEATURE:
<223> OTHER INFORMATION: primer

<400> SEQUENCE: 159
acgttggatg tgttcaaggg aaacagcatg                                   30

<210> SEQ ID NO 160
<211> LENGTH: 30
<212> TYPE: DNA
<213> ORGANISM: Artificial Sequence
<220> FEATURE:
<223> OTHER INFORMATION: primer

<400> SEQUENCE: 160
acgttggatg ggagtggaca aaatgtaaag                                   30

<210> SEQ ID NO 161
<211> LENGTH: 20
<212> TYPE: DNA
<213> ORGANISM: Artificial Sequence
<220> FEATURE:
<223> OTHER INFORMATION: primer

<400> SEQUENCE: 161
cagctcctag aaccaacaga                                              20

<210> SEQ ID NO 162
<211> LENGTH: 30
<212> TYPE: DNA
<213> ORGANISM: Artificial Sequence
<220> FEATURE:
<223> OTHER INFORMATION: primer

<400> SEQUENCE: 162
acgttggatg tggaaagaga ttgcactgcc                                   30

<210> SEQ ID NO 163
<211> LENGTH: 30
<212> TYPE: DNA
<213> ORGANISM: Artificial Sequence
<220> FEATURE:
<223> OTHER INFORMATION: primer

<400> SEQUENCE: 163
acgttggatg acaggctaat agcgtggttg                                   30

<210> SEQ ID NO 164
<211> LENGTH: 19
<212> TYPE: DNA
<213> ORGANISM: Artificial Sequence
<220> FEATURE:
<223> OTHER INFORMATION: primer

<400> SEQUENCE: 164
cctcaatgta acaaggaca                                               19

<210> SEQ ID NO 165
<211> LENGTH: 30
<212> TYPE: DNA
<213> ORGANISM: Artificial Sequence
<220> FEATURE:
<223> OTHER INFORMATION: primer

<400> SEQUENCE: 165
acgttggatg tgcctcttat ccaacatgag         30

<210> SEQ ID NO 166
<211> LENGTH: 30
<212> TYPE: DNA
<213> ORGANISM: Artificial Sequence
<220> FEATURE:
<223> OTHER INFORMATION: primer

<400> SEQUENCE: 166
acgttggatg ggtgaagaat ggcttaaaag         30

<210> SEQ ID NO 167
<211> LENGTH: 22
<212> TYPE: DNA
<213> ORGANISM: Artificial Sequence
<220> FEATURE:
<223> OTHER INFORMATION: primer

<400> SEQUENCE: 167
tcttatccaa catgagaatc ca         22

<210> SEQ ID NO 168
<211> LENGTH: 30
<212> TYPE: DNA
<213> ORGANISM: Artificial Sequence
<220> FEATURE:
<223> OTHER INFORMATION: primer

<400> SEQUENCE: 168
acgttggatg taaggctgag gacatgttgc         30

<210> SEQ ID NO 169
<211> LENGTH: 30
<212> TYPE: DNA
<213> ORGANISM: Artificial Sequence
<220> FEATURE:
<223> OTHER INFORMATION: primer

<400> SEQUENCE: 169
acgttggatg aaagaagtgg caaaggcagg         30

<210> SEQ ID NO 170
<211> LENGTH: 19
<212> TYPE: DNA
<213> ORGANISM: Artificial Sequence
<220> FEATURE:
<223> OTHER INFORMATION: primer

<400> SEQUENCE: 170
gctctgtctt tatatgaat         19

<210> SEQ ID NO 171
<211> LENGTH: 30
<212> TYPE: DNA
<213> ORGANISM: Artificial Sequence
<220> FEATURE:

<223> OTHER INFORMATION: primer

<400> SEQUENCE: 171
acgttggatg cttgcaccat tatcattgcc							30

<210> SEQ ID NO 172
<211> LENGTH: 30
<212> TYPE: DNA
<213> ORGANISM: Artificial Sequence
<220> FEATURE:
<223> OTHER INFORMATION: primer

<400> SEQUENCE: 172
acgttggatg tcttaatggt catgcgtggg							30

<210> SEQ ID NO 173
<211> LENGTH: 17
<212> TYPE: DNA
<213> ORGANISM: Artificial Sequence
<220> FEATURE:
<223> OTHER INFORMATION: primer

<400> SEQUENCE: 173
ttgccaattt gcagatg							17

<210> SEQ ID NO 174
<211> LENGTH: 31
<212> TYPE: DNA
<213> ORGANISM: Artificial Sequence
<220> FEATURE:
<223> OTHER INFORMATION: primer

<400> SEQUENCE: 174
acgttggatg gtctcataaa gcacaaccaa c							31

<210> SEQ ID NO 175
<211> LENGTH: 31
<212> TYPE: DNA
<213> ORGANISM: Artificial Sequence
<220> FEATURE:
<223> OTHER INFORMATION: primer

<400> SEQUENCE: 175
acgttggatg gtcacttggt tctaaatgtg g							31

<210> SEQ ID NO 176
<211> LENGTH: 20
<212> TYPE: DNA
<213> ORGANISM: Artificial Sequence
<220> FEATURE:
<223> OTHER INFORMATION: primer

<400> SEQUENCE: 176
aagcacaacc aactacatgc							20

<210> SEQ ID NO 177
<211> LENGTH: 30
<212> TYPE: DNA
<213> ORGANISM: Artificial Sequence
<220> FEATURE:
<223> OTHER INFORMATION: primer

<400> SEQUENCE: 177
acgttggatg actacaggaa gaagaaacag							30

```
<210> SEQ ID NO 178
<211> LENGTH: 30
<212> TYPE: DNA
<213> ORGANISM: Artificial Sequence
<220> FEATURE:
<223> OTHER INFORMATION: primer

<400> SEQUENCE: 178
acgttggatg ctctcgatca ctttggagac                              30

<210> SEQ ID NO 179
<211> LENGTH: 20
<212> TYPE: DNA
<213> ORGANISM: Artificial Sequence
<220> FEATURE:
<223> OTHER INFORMATION: primer

<400> SEQUENCE: 179
agaagaaaca gaaagtgtgt                                         20

<210> SEQ ID NO 180
<211> LENGTH: 30
<212> TYPE: DNA
<213> ORGANISM: Artificial Sequence
<220> FEATURE:
<223> OTHER INFORMATION: primer

<400> SEQUENCE: 180
acgttggatg gttgctacag agaacagaag                              30

<210> SEQ ID NO 181
<211> LENGTH: 30
<212> TYPE: DNA
<213> ORGANISM: Artificial Sequence
<220> FEATURE:
<223> OTHER INFORMATION: primer

<400> SEQUENCE: 181
acgttggatg gttctcccct tagattgacc                              30

<210> SEQ ID NO 182
<211> LENGTH: 19
<212> TYPE: DNA
<213> ORGANISM: Artificial Sequence
<220> FEATURE:
<223> OTHER INFORMATION: primer

<400> SEQUENCE: 182
gagaacagaa gtaaaacca                                          19

<210> SEQ ID NO 183
<211> LENGTH: 30
<212> TYPE: DNA
<213> ORGANISM: Artificial Sequence
<220> FEATURE:
<223> OTHER INFORMATION: primer

<400> SEQUENCE: 183
acgttggatg tgactgttgt tagcagaggc                              30

<210> SEQ ID NO 184
<211> LENGTH: 30
<212> TYPE: DNA
<213> ORGANISM: Artificial Sequence
<220> FEATURE:
<223> OTHER INFORMATION: primer
```

<400> SEQUENCE: 184
acgttggatg ggtaactctc atagccaagg    30

<210> SEQ ID NO 185
<211> LENGTH: 17
<212> TYPE: DNA
<213> ORGANISM: Artificial Sequence
<220> FEATURE:
<223> OTHER INFORMATION: primer

<400> SEQUENCE: 185
ttccagggga agctgtt    17

<210> SEQ ID NO 186
<211> LENGTH: 30
<212> TYPE: DNA
<213> ORGANISM: Artificial Sequence
<220> FEATURE:
<223> OTHER INFORMATION: primer

<400> SEQUENCE: 186
acgttggatg ttctccgtga ctgtttcagc    30

<210> SEQ ID NO 187
<211> LENGTH: 30
<212> TYPE: DNA
<213> ORGANISM: Artificial Sequence
<220> FEATURE:
<223> OTHER INFORMATION: primer

<400> SEQUENCE: 187
acgttggatg ggaaactacc ccacaagatg    30

<210> SEQ ID NO 188
<211> LENGTH: 17
<212> TYPE: DNA
<213> ORGANISM: Artificial Sequence
<220> FEATURE:
<223> OTHER INFORMATION: primer

<400> SEQUENCE: 188
tgtttcagct ctgcccc    17

<210> SEQ ID NO 189
<211> LENGTH: 30
<212> TYPE: DNA
<213> ORGANISM: Artificial Sequence
<220> FEATURE:
<223> OTHER INFORMATION: primer

<400> SEQUENCE: 189
acgttggatg gtctcccgag gagagaaatt    30

<210> SEQ ID NO 190
<211> LENGTH: 31
<212> TYPE: DNA
<213> ORGANISM: Artificial Sequence
<220> FEATURE:
<223> OTHER INFORMATION: primer

<400> SEQUENCE: 190
acgttggatg ccctgaagtc taaataagat g    31

<210> SEQ ID NO 191
<211> LENGTH: 20

<212> TYPE: DNA
<213> ORGANISM: Artificial Sequence
<220> FEATURE:
<223> OTHER INFORMATION: primer

<400> SEQUENCE: 191
tccttttagc ctagaagagc                                          20

<210> SEQ ID NO 192
<211> LENGTH: 30
<212> TYPE: DNA
<213> ORGANISM: Artificial Sequence
<220> FEATURE:
<223> OTHER INFORMATION: primer

<400> SEQUENCE: 192
acgttggatg gggaagactt aagcagaaac                               30

<210> SEQ ID NO 193
<211> LENGTH: 30
<212> TYPE: DNA
<213> ORGANISM: Artificial Sequence
<220> FEATURE:
<223> OTHER INFORMATION: primer

<400> SEQUENCE: 193
acgttggatg caatgcccag atgctcaatc                               30

<210> SEQ ID NO 194
<211> LENGTH: 17
<212> TYPE: DNA
<213> ORGANISM: Artificial Sequence
<220> FEATURE:
<223> OTHER INFORMATION: primer

<400> SEQUENCE: 194
tatttctctg taggggg                                             17

<210> SEQ ID NO 195
<211> LENGTH: 30
<212> TYPE: DNA
<213> ORGANISM: Artificial Sequence
<220> FEATURE:
<223> OTHER INFORMATION: primer

<400> SEQUENCE: 195
acgttggatg atactacagt cctgacagag                               30

<210> SEQ ID NO 196
<211> LENGTH: 30
<212> TYPE: DNA
<213> ORGANISM: Artificial Sequence
<220> FEATURE:
<223> OTHER INFORMATION: primer

<400> SEQUENCE: 196
acgttggatg acttcttccc tccaaacctc                               30

<210> SEQ ID NO 197
<211> LENGTH: 22
<212> TYPE: DNA
<213> ORGANISM: Artificial Sequence
<220> FEATURE:
<223> OTHER INFORMATION: primer

<400> SEQUENCE: 197

```
tacagtcctg acagagtaaa at                                              22

<210> SEQ ID NO 198
<211> LENGTH: 30
<212> TYPE: DNA
<213> ORGANISM: Artificial Sequence
<220> FEATURE:
<223> OTHER INFORMATION: primer

<400> SEQUENCE: 198
acgttggatg gctcactctt ctcaccaatg                                      30

<210> SEQ ID NO 199
<211> LENGTH: 30
<212> TYPE: DNA
<213> ORGANISM: Artificial Sequence
<220> FEATURE:
<223> OTHER INFORMATION: primer

<400> SEQUENCE: 199
acgttggatg gttgccgagg catttgaaag                                      30

<210> SEQ ID NO 200
<211> LENGTH: 17
<212> TYPE: DNA
<213> ORGANISM: Artificial Sequence
<220> FEATURE:
<223> OTHER INFORMATION: primer

<400> SEQUENCE: 200
ggctgcttcc cctccca                                                    17
```

POLYNUCLEOTIDE ASSOCIATED WITH A TYPE II DIABETES MELLITUS COMPRISING SINGLE NUCLEOTIDE POLYMORPHISM, MICROARRAY AND DIAGNOSTIC KIT COMPRISING THE SAME AND METHOD FOR ANALYZING POLYNUCLEOTIDE USING THE SAME

1. FIELD OF THE INVENTION

The present invention relates to a polynucleotide associated with type II diabetes mellitus, a microarray and a diagnostic kit including the same, and a method of analyzing polynucleotides associated with type II diabetes mellitus.

2. DESCRIPTION OF THE RELATED ART

The genomes of all organisms undergo spontaneous mutation in the course of their continuing evolution, generating variant forms of progenitor nucleic acid sequences (Gusella, Ann. Rev. Biochem. 55, 831-854 (1986)). The variant forms may confer an evolutionary advantage or disadvantage, relative to a progenitor form, or may be neutral. In some instances, a variant form confers a lethal disadvantage and is not transmitted to subsequent generations of the organism. In other instances, a variant form confers an evolutionary advantage to the species and is eventually incorporated into the DNA of most members of the species and effectively becomes the progenitor form. In many instances, both progenitor and variant form(s) survive and co-exist in a species population. The coexistence of multiple forms of a sequence gives rise to polymorphisms.

Several different types of polymorphisms have been known, including restriction fragment length polymorphisms (RFLPs), short tandem repeats (STRs), variable number tandem repeats (VNTRs) and single-nucleotide polymorphisms (SNPs). Among them, SNPs take the form of single-nucleotide variations between individuals of the same species. When SNPs occur in protein coding sequences, any one of the polymorphic forms may give rise to the expression of a defective or a variant protein. On the other hand, when SNPs occur in non-coding sequences, some of these polymorphisms may result in the expression of defective or variant proteins (e.g., as a result of defective splicing). Other SNPs have no phenotypic effects.

It is known that human SNPs occur at a frequency of 1 in about 1,000 bp. When such SNPs induce a phenotypic expression such as a disease, polynucleotides containing the SNPs can be used as primers or probes for diagnosis of a disease. Monoclonal antibodies specifically binding with the SNPs can also be used in diagnosis of a disease. Currently, research into the nucleotide sequences and functions of SNPs is under way by many research institutes. The nucleotide sequences and other experimental results of the identified human SNPs have been made into database to be easily accessible.

Even though findings available to date show that specific SNPs exist on human genomes or cDNAs, phenotypic effects of such SNPs have not been revealed. Functions of most SNPs have not been disclosed yet except some SNPs.

It is known that 90-95% of total diabetes patients suffer type II diabetes mellitus. Type II diabetes mellitus is a disorder which is developed in persons who abnormally produce insulin or have low sensitivity to insulin, thereby resulting in large change in blood glucose level. When disorder of insulin secretion leads to the condition of type II diabetes mellitus, blood glucose cannot be transferred to body cells, which renders the conversion of food into energy difficult. It is known that a genetic cause has a role in type II diabetes mellitus. Other risk factors of type II diabetes mellitus are age over 45, familial history of diabetes mellitus, obesity, hypertension, and high cholesterol level. Currently, diagnosis of diabetes mellitus is mainly made by measuring a pathological phenotypic change, i.e., blood glucose level, using fasting blood glucose (FSB) test, oral glucose tolerance test (OGTT), and the like [National Institute of Diabetes and Digestive and Kidney Diseases of the National Institutes of Health, 2003]. When diagnosis of type II diabetes mellitus is made, type II diabetes mellitus can be prevented or its onset can be delayed by exercise, special diet, body weight control, drug therapy, and the like. In this regard, it can be said that type II diabetes mellitus is a disease in which early diagnosis is highly desirable. Millenium Pharmaceuticals Inc. reported that diagnosis and prognosis of type II diabetes mellitus can be made based on genotypic variations present on HNF1 gene [PR newswire, Sep. 1, 1998]. Sequenom Inc. reported that FOXA2 (HNF3β) gene is highly associated with type II diabetes mellitus [PR Newswire, Oct. 28, 2003]. Even though there are reports about some genes associated with type II diabetes mellitus, researches into the incidence of type II diabetes mellitus have been focused on specific genes of some chromosomes in specific populations. For this reason, research results may vary according to human species. Furthermore, all causative genes responsible for type II diabetes mellitus have not yet been identified. Diagnosis of type II diabetes mellitus by such a molecular biological technique is now uncommon. In addition, early diagnosis before incidence of type II diabetes mellitus is currently unavailable. Therefore, there is an increasing need to find new SNPs highly associated with type II diabetes mellitus and related genes that are found in whole human genomes and to make early diagnosis of type II diabetes mellitus using the SNPs and the related genes.

SUMMARY OF THE INVENTION

The present invention provides a polynucleotide containing single-nucleotide polymorphism associated with type II diabetes mellitus.

The present invention also provides a microarray and a type II diabetes mellitus diagnostic kit, each of which includes the polynucleotide containing single-nucleotide polymorphism associated with type II diabetes mellitus.

The present invention also provides a method of analyzing polynucleotides associated with type II diabetes mellitus.

DETAILED DESCRIPTION OF THE INVENTION

The present invention provides a polynucleotide for diagnosis or treatment of type II diabetes mellitus, including at least 10 contiguous nucleotides of a nucleotide sequence selected from the group consisting of nucleotide sequences of SEQ ID NOS: 1-80 and including a nucleotide of a polymorphic site (position 101) of the nucleotide sequence, or a complementary polynucleotide thereof.

The polynucleotide includes a contiguous span of at least 10 nucleotides containing the polymorphic site of a nucleotide sequence selected from the nucleotide sequences of SEQ ID NOS: 1-80. The polynucleotide is 10 to 400 nucleotides in length, preferably 10 to 100 nucleotides in length, and more preferably 10 to 50 nucleotides in length. Here, the polymorphic site of each nucleotide sequence of SEQ ID NOS: 1-80 is at position 101.

Each of the nucleotide sequences of SEQ ID NOS: 1-80 is a polymorphic sequence. The polymorphic sequence refers to a nucleotide sequence containing a polymorphic site at which single-nucleotide polymorphism (SNP) occurs. The polymorphic site refers to a position of a polymorphic sequence at which SNP occurs. The nucleotide sequences may be DNAs or RNAs.

In the present invention, the polymorphic sites (position 101) of the polymorphic sequences of SEQ ID NOS: 1-80 are associated with type II diabetes mellitus. This is confirmed by DNA sequence analysis of blood samples derived from type II diabetes mellitus patients and normal persons. Association of the polymorphic sequences of SEQ ID NOS: 1-80 with type II diabetes mellitus and characteristics of the polymorphic sequences are summarized in Tables 1-1, 1-2, 2-1, and 2-2.

TABLE 1-1

| ASSAY_ID | SNP | SNP sequence (SEQ ID NO.) | Allele frequency | | | Genotype frequency | | |
|---|---|---|---|---|---|---|---|---|
| | | | cas_A2 | con_A2 | Delta | cas_A1A1 | cas_A1A2 | cas_A2A2 |
| DMX_001 | C→T | 1 and 2 | 0.592 | 0.492 | 0.1 | 54 | 136 | 109 |
| DMX_003 | A→G | 3 and 4 | 0.292 | 0.202 | 0.09 | 157 | 108 | 33 |
| DMX_005 | A→G | 5 and 6 | 0.871 | 0.913 | 0.042 | 3 | 71 | 224 |
| DMX_008 | G→A | 7 and 8 | 0.218 | 0.158 | 0.06 | 180 | 103 | 13 |
| DMX_009 | T→G | 9 and 10 | 0.664 | 0.737 | 0.073 | 31 | 138 | 129 |
| DMX_011 | A→G | 11 and 12 | 0.866. | 0.931 | 0.065 | 7 | 66 | 225 |
| DMX_012 | C→G | 13 and 14 | 0.527 | 0.614 | 0.087 | 72 | 140 | 88 |
| DMX_014 | A→C | 15 and 16 | 0.903 | 0.837 | 0.066 | 0 | 58 | 240 |
| DMX_016 | A→G | 17 and 18 | 0.275 | 0.209 | 0.066 | 158 | 116 | 24 |
| DMX_019 | T→C | 19 and 20 | 0.961 | 0.924 | 0.037 | 1 | 21 | 275 |
| DMX_027 | G→C | 21 and 22 | 0.844 | 0.89 | 0.046 | 3 | 87 | 208 |
| DMX_028 | T→C | 23 and 24 | 0.945 | 0.977 | 0.032 | 0 | 33 | 266 |
| DMX_029 | C→A | 25 and 26 | 0.057 | 0.104 | 0.047 | 268 | 28 | 3 |
| DMX_030 | C→T | 27 and 28 | 0.077 | 0.129 | 0.052 | 251 | 41 | 2 |
| DMX_031 | A→T | 29 and 30 | 0.916 | 0.86 | 0.056 | 2 | 46 | 251 |
| DMX_032 | T→A | 31 and 32 | 0.718 | 0.593 | 0.125 | 26 | 117 | 157 |
| DMX_033 | T→C | 33 and 34 | 0.816 | 0.9 | 0.084 | 10 | 89 | 198 |
| DMX_044 | A→T | 35 and 36 | 0.846 | 0.787 | 0.059 | 7 | 78 | 213 |
| DMX_049 | T→A | 37 and 38 | 0.107 | 0.06 | 0.047 | 236 | 60 | 2 |
| DMX_052 | C→T | 39 and 40 | 0.94 | 0.907 | 0.033 | 3 | 29 | 261 |

| ASSAY_ID | Genotype frequency | | | df = 2 | |
|---|---|---|---|---|---|
| | con_A1A1 | con_A1A2 | con_A2A2 | Chi_value | Chi_exact_p-Value |
| DMX_001 | 77 | 151 | 72 | 12.384 | 2.05E-03 |
| DMX_003 | 190 | 97 | 12 | 13.527 | 1.16E-03 |
| DMX_005 | 4 | 44 | 251 | 8.015 | 1.82E-02 |
| DMX_008 | 205 | 80 | 6 | 7.051 | 2.94E-02 |
| DMX_009 | 19 | 119 | 161 | 7.814 | 2.01E-02 |
| DMX_011 | 1 | 39 | 258 | 13.698 | 1.06E-03 |
| DMX_012 | 44 | 139 | 111 | 9.361 | 9.28E-03 |
| DMX_014 | 10 | 77 | 211 | 14.539 | 6.97E-04 |
| DMX_016 | 182 | 95 | 13 | 6.947 | 3.10E-02 |
| DMX_019 | 2 | 41 | 254 | 7.619 | 2.22E-02 |
| DMX_027 | 3 | 60 | 237 | 6.842 | 3.27E-02 |
| DMX_028 | 0 | 14 | 284 | 8.268 | 5.72E-03 |
| DMX_029 | 241 | 52 | 5 | 9.131 | 1.04E-02 |
| DMX_030 | 221 | 70 | 3 | 9.683 | 7.89E-03 |
| DMX_031 | 6 | 72 | 221 | 9.636 | 8.08E-03 |
| DMX_032 | 51 | 142 | 107 | 20 | 4.54E-05 |
| DMX_033 | 4 | 51 | 239 | 16.718 | 2.34E-04 |
| DMX_044 | 15 | 93 | 181 | 6.687 | 3.53E-02 |
| DMX_049 | 263 | 36 | 0 | 9.459 | 8.83E-03 |
| DMX_052 | 1 | 52 | 238 | 8.584 | 1.37E-02 |

| Odds ratio (OR): multiple model | | | | | | | |
|---|---|---|---|---|---|---|---|
| Risk allele | | OR | CI | HWE | | Sample call rate | |
| | | | | con_HW | cas_HW | cas_call_rate | con_call_rate |
| A2 | T | 1.49 | (1.193, 1.887) | .027, HWE | 1.195, HWE | 1 | 1 |
| A2 | G | 1.61 | (1.245, 2.123) | .01, HWE | 4.819, HWE | 0.99 | 1 |
| A1 | A | 1.56 | (1.074, 2.259) | 2.208, HWE | .646, HWE | 0.99 | 1 |
| A2 | A | 1.49 | (1.104, 1.996) | .265, HWE | .167, HWE | 0.99 | 0.97 |
| A1 | T | 1.42 | (1.106, 1.82) | .195, HWE | .424, HWE | 0.99 | 1 |
| A1 | A | 2.10 | (1.414, 3.115) | .026, HWE | .948, HWE | 0.99 | 0.99 |
| A1 | C | 1.43 | (1.135, 1.8) | .032, HWE | 1.218, HWE | 1 | 0.98 |
| A2 | C | 1.82 | (1.274, 2.551) | 1.527, HWE | 1.834, HWE | 0.99 | 0.99 |
| A2 | G | 1.45 | (1.1, 1.883) | .089, HWE | .241, HWE | 0.99 | 0.97 |
| A2 | C | 2.04 | (1.215, 3.413) | 1.004, HWE | .549, HWE | 0.99 | 0.99 |

TABLE 1-1-continued

| | | | | | | | |
|---|---|---|---|---|---|---|---|
| A1 | G | 1.50 | (1.067, 2.098) | .069, HWE | 3.4, HWE | 0.99 | 1 |
| A1 | T | 2.43 | (1.286, 4.585) | .077, HWE | .133, HWE | 1 | 0.99 |
| A1 | C | 1.93 | (1.247, 2.975) | 1.514, HWE | HWD | 1 | 0.99 |
| A1 | C | 1.79 | (1.215, 2.64) | .51, HWE | 1.004, HWE | 0.98 | 0.98 |
| A2 | T | 1.79 | (1.238, 2.591) | .214, HWE | .004, HWE | 1 | 1 |
| A2 | A | 1.75 | (1.374, 2.227) | .148, HWE | .582, HWE | 1 | 1 |
| A1 | T | 2.02 | (1.434, 2.831) | 2.023, HWE | .005, HWE | 0.99 | 0.98 |
| A2 | T | 1.47 | (1.099, 1.996) | .452, HWE | .013, HWE | 0.99 | 0.96 |
| A2 | G | 1.89 | (1.227, 2.874) | .527, HWE | .623, HWE | 0.99 | 1 |
| A2 | T | 1.61 | (1.035, 2.506) | .688, HWE | 4.52, HWE | 0.98 | 0.97 |

TABLE 1-2

| ASSAY_ID | SNP | SNP sequence (SEQ ID NO.) | Allele frequency | | | Genotype frequency | | |
|---|---|---|---|---|---|---|---|---|
| | | | cas_A2 | con_A2 | Delta | cas_A1A1 | cas_A1A2 | cas_A2A2 |
| DMX_054 | C→A | 41 and 42 | 0.14 | 0.09 | 0.05 | 222 | 70 | 7 |
| DMX_056 | A→G | 43 and 44 | 0.362 | 0.273 | 0.089 | 123 | 137 | 40 |
| DMX_060 | G→A | 45 and 46 | 0.957 | 0.925 | 0.032 | 0 | 25 | 267 |
| DMX_061 | T→C | 47 and 48 | 0.758 | 0.81 | 0.052 | 11 | 121 | 164 |
| DMX_062 | C→T | 49 and 50 | 0.421 | 0.508 | 0.087 | 106 | 133 | 59 |
| DMX_063 | G→C | 51 and 52 | 0.902 | 0.953 | 0.051 | 2 | 55 | 243 |
| DMX_065 | C→T | 53 and 54 | 0.92 | 0.958 | 0.038 | 4 | 39 | 250 |
| DMX_067 | G→A | 55 and 56 | 0.903 | 0.941 | 0.038 | 2 | 54 | 243 |
| DMX_068 | A→G | 57 and 58 | 0.081 | 0.133 | 0.052 | 252 | 42 | 3 |
| DMX_069 | T→C | 59 and 60 | 0.44 | 0.498 | 0.058 | 96 | 143 | 60 |
| DMX_104 | T→C | 61 and 62 | 0.274 | 0.204 | 0.07 | 158 | 115 | 24 |
| DMX_105 | A→C | 63 and 64 | 0.769 | 0.838 | 0.069 | 19 | 100 | 180 |
| DMX_116 | T→C | 65 and 66 | 0.6 | 0.668 | 0.068 | 41 | 157 | 101 |
| DMX_117 | T→C | 67 and 68 | 0.188 | 0.251 | 0.063 | 199 | 89 | 12 |
| DMX_120 | A→G | 69 and 70 | 0.818 | 0.871 | 0.053 | 7 | 95 | 197 |
| DMX_136 | T→C | 71 and 72 | 0.211 | 0.263 | 0.052 | 188 | 96 | 15 |
| DMX_139 | A→G | 73 and 74 | 0.17 | 0.105 | 0.065 | 205 | 88 | 7 |
| DMX_150 | A→G | 75 and 76 | 0.926 | 0.958 | 0.032 | 0 | 44 | 252 |
| DMX_152 | A→C | 77 and 78 | 0.562 | 0.64 | 0.078 | 62 | 136 | 99 |
| DMX_154 | A→G | 79 and 80 | 0.269 | 0.199 | 0.07 | 153 | 131 | 15 |

| ASSAY_ID | Genotype frequency | | | df = 2 | |
|---|---|---|---|---|---|
| | con_A1A1 | con_A1A2 | con_A2A2 | Chi_value | Chi_exact_p-Value |
| DMX_054 | 248 | 48 | 3 | 7.14 | 2.82E−02 |
| DMX_056 | 160 | 116 | 24 | 10.581 | 5.04E−03 |
| DMX_060 | 3 | 39 | 257 | 6.171 | 4.57E−02 |
| DMX_061 | 13 | 87 | 198 | 8.911 | 1.16E−02 |
| DMX_062 | 72 | 146 | 77 | 9.468 | 8.79E−03 |
| DMX_063 | 1 | 26 | 272 | 12.347 | 2.08E−03 |
| DMX_065 | 0 | 24 | 263 | 7.84 | 1.98E−02 |
| DMX_067 | 2 | 31 | 264 | 7.087 | 2.89E−02 |
| DMX_068 | 227 | 59 | 10 | 7.934 | 1.89E−02 |
| DMX_069 | 66 | 164 | 65 | 7.165 | 2.78E−02 |
| DMX_104 | 184 | 95 | 12 | 7.821 | 2.00E−02 |
| DMX_105 | 9 | 79 | 212 | 8.646 | 1.33E−02 |
| DMX_116 | 29 | 139 | 129 | 6.554 | 3.77E−02 |
| DMX_117 | 171 | 103 | 23 | 6.582 | 3.72E−02 |
| DMX_120 | 3 | 70 | 222 | 6.853 | 3.25E−02 |
| DMX_136 | 156 | 123 | 16 | 6.311 | 4.26E−02 |
| DMX_139 | 239 | 59 | 2 | 11.102 | 3.88E−03 |
| DMX_150 | 0 | 25 | 270 | 5.851 | 2.06E−02 |
| DMX_152 | 41 | 129 | 123 | 7.034 | 2.97E−02 |
| DMX_154 | 187 | 100 | 9 | 9.045 | 1.09E−02 |

Odds ratio (OR): multiple model

| Risk allele | OR | CI | HWE | | Sample call rate | |
|---|---|---|---|---|---|---|
| | | | con_HW | cas_HW | cas_call_rate | con_call_rate |
| A2 | A | 1.64 | (1.145, 2.364) | .504, HWE | .819, HWE | 1 | 1 |
| A2 | G | 1.52 | (1.179, 1.923) | .283, HWE | .041, HWE | 1 | 1 |
| A2 | A | 1.82 | (1.1, 3.012) | 4.113, HWE | .042, HWE | 0.97 | 1 |

TABLE 1-2-continued

| | | | | | | | |
|---|---|---|---|---|---|---|---|
| A1 | T | 1.36 | (1.031, 1.798) | 1.122, HWE | 3.894, HWE | 0.99 | 0.99 |
| A1 | C | 1.42 | (1.131, 1.788) | .034, HWE | 2.43, HWE | 0.99 | 0.98 |
| A1 | G | 2.22 | (1.395, 3.534) | .504, HWE | .08, HWE | 1 | 1 |
| A1 | C | 2.00 | (1.205, 3.314) | .043, HWE | 9.409, HWE | 0.98 | 0.96 |
| A1 | G | 1.72 | (1.109, 2.653) | 1.047, HWE | .077, HWE | 1 | 0.99 |
| A1 | A | 1.75 | (1.2, 2.557) | 6.304, HWE | 4.107, HWE | 0.99 | 0.99 |
| A1 | T | 1.27 | (1.007, 1.59) | 3.708, HWE | .364, HWE | 1 | 0.98 |
| A2 | C | 1.47 | (1.122, 1.927) | .011, HWE | .284, HWE | 0.99 | 0.97 |
| A1 | A | 1.56 | (1.165, 2.077) | .64, HWE | 1.497, HWE | 1 | 1 |
| A1 | T | 1.34 | (1.059, 1.7) | .838, HWE | 2.473, HWE | 1 | 0.99 |
| A1 | T | 1.44 | (1.095, 1.902) | 2.116, HWE | .464, HWE | 1 | 0.99 |
| A1 | A | 1.51 | (1.097, 2.072) | .497, HWE | .894, HWE | 1 | 0.98 |
| A1 | T | 1.33 | (1.02, 1.746) | 1.611, HWE | .42, HWE | 1 | 0.98 |
| A2 | G | 1.75 | (1.247, 2.445) | .498, HWE | .32, HWE | 1 | 1 |
| A1 | A | 1.81 | (1.095, 3.006) | .174, HWE | .654, HWE | 0.99 | 0.98 |
| A1 | A | 1.38 | (1.095, 1.748) | .774, HWE | 1.715, HWE | 0.99 | 0.98 |
| A2 | G | 1.47 | (1.129, 1.942) | .768, HWE | 3.616, HWE | 1 | 0.99 |

TABLE 2-1

| ASSAY_ID | rs | SNP site | SNP sequence (SEQ ID NO) | Chromosome # | Chromosome position | Band | Gene |
|---|---|---|---|---|---|---|---|
| DMX_001 | rs502612 | C→T | 1 and 2 | 1 | 167373461 | 1q24.2 | PRRX1 |
| DMX_003 | rs1483 | A→G | 3 and 4 | 1 | 223672376 | 1q42.13 | CDC42BPA |
| DMX_005 | rs632585 | A→G | 5 and 6 | 1 | 228802209 | 1q42.2 | between genes |
| DMX_008 | rs177560 | G→A | 7 and 8 | 11 | 16911751 | 11p15.1 | between genes |
| DMX_009 | rs1394720 | T→G | 9 and 10 | 11 | 4533242 | 11p15.4 | between genes |
| DMX_011 | rs488115 | A→G | 11 and 12 | 11 | 74409538 | 11q13.4 | between genes |
| DMX_012 | rs2063728 | C→G | 13 and 14 | 11 | 77863284 | 11q14.1 | FLJ23441 |
| DMX_014 | rs725834 | A→C | 15 and 16 | 13 | 99254859 | 13q32.3 | CLYBL |
| DMX_016 | rs767837 | A→G | 17 and 18 | 13 | 48218663 | 13q14.2 | between genes |
| DMX_019 | rs929703 | T→C | 19 and 20 | 14 | 77691031 | 14q24.3 | between genes |
| DMX_027 | rs739637 | G→C | 21 and 22 | 17 | 37534470 | 17q21.2 | RAB5C |
| DMX_028 | rs1990936 | T→C | 23 and 24 | 17 | 44307486 | 17q21.32 | between genes |
| DMX_029 | rs2051672 | C→A | 25 and 26 | 17 | 5847149 | 17p13.2 | between genes |
| DMX_030 | rs1038308 | C→T | 27 and 28 | 18 | 44038585 | 18q21.1 | KIAA0427 |
| DMX_031 | rs655080 | A→T | 29 and 30 | 18 | 57917416 | 18q21.33 | PIGN |
| DMX_032 | rs1943317 | T→A | 31 and 32 | 18 | 62419479 | 18q22.1 | between genes |
| DMX_033 | rs929476 | T→C | 33 and 34 | 19 | 33499519 | 19q12 | between genes |
| DMX_044 | rs1984388 | A→T | 35 and 36 | 22 | 30658575 | 22q12.3 | between genes |
| DMX_049 | rs1707709 | T→G | 37 and 38 | 3 | 166922235 | 3q26.1 | between genes |
| DMX_052 | rs1786 | C→T | 39 and 40 | 4 | 15340722 | 4p15.33 | between genes |

| Description | SNP function | Amino acid change | Remarks |
|---|---|---|---|
| Paired related homeobox 1 | Intron | No change | |
| CDC42 binding protein kinase alpha (DMPK45 analogue) | Intron | No change | |
| — | Between genes | No change | |
| — | Between genes | No change | |
| — | Between genes | No change | |
| — | Between genes | No change | |
| Imaginary protein FLJ23441 | Intron | No change | |
| Citrate lyase beta analogue | Intron | No change | |
| — | Between genes | No change | |
| — | Between genes | No change | |
| RAB5C, RAS oncogene family | Intron | No change | |
| — | Between genes | No change | |
| — | Between genes | No change | |
| KIAA0427 | Coding-synon | No change | |
| Phosphatidylinositol glycan, class N | Intron | No change | |
| — | Between genes | No change | |
| — | Between genes | No change | |
| — | Between genes | No change | |
| — | Between genes | No change | |
| — | Between genes | No change | |

TABLE 2-2

| ASSAY_ID | rs | SNP site | SNP sequence (SEQ ID NO) | Chromosome # | Chromosome position | Band | Gene |
|---|---|---|---|---|---|---|---|
| DMX_054 | rs872883 | C→A | 41 and 42 | 4 | 6582619 | 4p16.1 | PPP2R2C |
| DMX_056 | rs752139 | A→G | 43 and 44 | 5 | 175943870 | 5q35.2 | PC-LKC |

TABLE 2-2-continued

| | | | | | | | |
|---|---|---|---|---|---|---|---|
| DMX_060 | rs1769972 | G→A | 45 and 46 | 6 | 106782512 | 6q21 | APG5L |
| DMX_061 | rs1322532 | T→C | 47 and 48 | 6 | 19175693 | 6p22.3 | Between genes |
| DMX_062 | rs2058501 | C→T | 49 and 50 | 7 | 120274187 | 7q31.31 | FLJ21986 |
| DMX_063 | rs1563047 | G→C | 51 and 52 | 7 | 134030698 | 7q33 | CALD1 |
| DMX_065 | rs38809 | C→T | 53 and 54 | 7 | 91792235 | 7q21.2 | PEX1 |
| DMX_067 | rs1054748 | G→A | 55 and 56 | 8 | 37837626 | 8p12 | RAB11FIP |
| DMX_068 | rs1434940 | A→G | 57 and 58 | 8 | 69660204 | 8q13.3 | VEST1 |
| DMX_069 | rs1059033 | T→C | 59 and 60 | 9 | 77736025 | 9q21.2 | GNAQ |
| DMX_104 | rs492220 | T→C | 61 and 62 | 1 | 94254590 | 1p22.1 | ABCA4 |
| DMX_105 | rs685328 | A→C | 63 and 64 | 10 | 117138050 | 10q25.3 | ATRNL1 |
| DMX_116 | rs1461986 | T→C | 65 and 66 | 13 | 75506683 | 13q22.2 | Between genes |
| DMX_117 | rs1815620 | T→C | 67 and 68 | 14 | 50995615 | 14q22.1 | Between genes |
| DMX_120 | rs293398 | A→G | 69 and 70 | 15 | 87459425 | 15q26.1 | ABHD2 |
| DMX_136 | rs1686492 | T→C | 71 and 72 | 2 | 10915411 | 2p25.1 | Between genes |
| DMX_139 | rs1237905 | A→G | 73 and 74 | 2 | 168278137 | 2q24.3 | Between genes |
| DMX_150 | rs589682 | A→G | 75 and 76 | 3 | 122172648 | 3q13.33 | STXBP5L |
| DMX_152 | rs607209 | A→C | 77 and 78 | 4 | 16808165 | 4p15.32 | Between genes |
| DMX_154 | rs197367 | A→G | 79 and 60 | 7 | 36219096 | 7p14.2 | ANLN |

| Description | SNP function | Amino acid change | Remarks |
|---|---|---|---|
| Protein phosphatase 2 (former 2A), regulatory subunit B (PR 52), gamma isoform | Intron | No change | |
| Protocadherin LKC | Intron | No change | |
| APG5 autophagy 545 analogue (*S. cerevisiae*) | Intron | No change | |
| — | Between genes | No change | |
| Imaginary protein FLJ21986 | Intron | No change | |
| Caldesmon 1 | Intron | No change | |
| Peroxisome biogenesis factor 1 | Intron | No change | |
| RAB11 family interaction protein 1 (class I) | No classified | No change | Between genes in |
| Vestibule-1 protein | Intron | No change | NCBI bulid 119 |
| Guanine nucleotide binding protein (G protein), q polypeptide | Intron | No change | |
| ATP45; binding cassette, sub45; family A (ABC1), member 4 | Intron | No change | |
| Attractin45 analogue 1 | Intron | No change | KIAA0534 in NCBI |
| — | Between genes | No change | build 119 |
| — | Between genes | No change | |
| 2-containing abhydrolase domain | mma-utr | No change | |
| — | Between genes | No change | |
| — | Between genes | No change | |
| Syntaxin binding protein 545 analogue | Intron | No change | KIAA 1006 in NCBI |
| — | Between genes | No change | build 119 |
| Anillin, actin binding protein (scraps homolog, Drosophila) | coding-nonsynon | K→R | |

In Tables 1-1 and 1-2, the contents in columns are as defined below.

Assay_ID represents a marker name.

SNP is a polymorphic base of a SNP polymorphic site. Here, A1 and A2 represent respectively a low mass allele and a high mass allele as a result of sequence analysis according a homogeneous MassExtension (hME) technique (Sequenom) and are optionally designated for convenience of experiments.

SNP sequence represents a sequence containing a SNP site, i.e., a sequence containing allele A1 or A2 at position 101.

At the allele frequency column, cas_A2, con_A2, and Delta respectively represent allele A2 frequency of a case group, allele A2 frequency of a normal group, and the absolute value of the difference between cas_A2 and con_A2. Here, cas_A2 is (genotype A2A2 frequency× 2+genotype A1A2 frequency)/(the number of samples× 2) in the case group and con_A2 is (genotype A2A2 frequency×2+genotype A1A2 frequency)/(the number of samples×2) in the normal group.

Genotype frequency represents the frequency of each genotype. Here, cas_A1A1, cas_A1A2, and cas_A2A2 are the number of persons with genotypes A1A1, A1A2, and A2A2, respectively, in the case group, and con_A1A1, con_A1A2, and con_A2A2 are the number of persons with genotypes A1A1, A1A2, and A2A2, respectively, in the normal group.

df=2 represents a chi-squared value with two degree of freedom. Chi-value represents a chi-squared value and p-value is determined based on the chi-value. Chi_exact_p-value represents p-value of Fisher's exact test of chi-square test. When the number of genotypes is less than 5, results of the chi-square test may be inaccurate. In this respect, determination of more accurate statistical significance (p-value) by the Fisher's exact test is required. The chi_exact_p-value is a variable used in the Fisher's exact test. In the present invention, when the p-value$\leq 0.05$, it is considered that the genotype of the case group is different from that of the normal group, i.e., there is a significant difference between the case group and the normal group.

At the risk allele column, when a reference allele is A2 and the allele A2 frequency of the case group is larger than the allele A2 frequency of the normal group (i.e., cas_A2>con_A2), the allele A2 is regarded as risk allele. In an opposite case, allele A1 is regarded as risk allele.

Odds ratio represents the ratio of the probability of risk allele in the case group to the probability of risk allele in the normal group. In the present invention, the Mantel- Haenszel odds ratio method was used. CI represents 95% confidence interval for the odds ratio and is represented by (lower limit of the confidence interval, upper limit of the confidence interval). When 1 falls under the confidence interval, it is considered that there is insignificant association of risk allele with disease.

HWE represents Hardy-Weinberg Equilibrium. Here, con_HWE and cas_HWE represent degree of deviation from the Hardy-Weinberg Equilibrium in the normal group and the case group, respectively. Based on chi_value=6.63 (p-value=0.01, df=1) in a chi-square (df=1) test, a value larger than 6.63 was regarded as Hardy-Weinberg Disequilibrium (HWD) and a value smaller than 6.63 was regarded as Hardy-Weinberg Equilibrium (HWE).

Call rate represents the number of genotype-interpretable samples to the total number of samples used in experiments. Here, cas_call_rate and con_call_rate represent the ratio of the number of genotype-interpretable samples to the total number (300 persons) of samples used in the case group and the normal group, respectively.

Tables 2-1 and 2-2 present characteristics of SNP markers based on the NCBI build 123.

As shown in Tables 1-1, 1-2, 2-1, and 2-2, according to the chi-square test of the polymorphic markers of SEQ ID NOS: 1-80 of the present invention, chi_exact_p-value ranges from $4.54 \times 10^{-4}$ to 0.0104 in 95% confidence interval. This shows that there are significant differences between expected values and measured values in allele occurrence frequencies in the polymorphic markers of SEQ ID NOS: 1-80. Odds ratio ranges from 1.34 to 2.43, which shows that the polymorphic markers of SEQ ID NOS: 1-80 are associated with type II diabetes mellitus.

The SNPs of SEQ ID NOS: 1-80 of the present invention occur at a significant frequency in a type II diabetic patient group and a normal group. Therefore, the polynucleotide according to the present invention can be efficiently used in diagnosis, fingerprinting analysis, or treatment of type II diabetes mellitus. In detail, the polynucleotide of the present invention can be used as a primer or a probe for diagnosis of type II diabetes mellitus. Furthermore, the polynucleotide of the present invention can be used as antisense DNA or a composition for treatment of type II diabetes mellitus.

The present invention also provides an allele-specific polynucleotide for diagnosis of type II diabetes mellitus, which is hybridized with a polynucleotide including a contiguous span of at least 10 nucleotides containing a nucleotide of a polymorphic site of a nucleotide sequence selected from the group consisting of the nucleotide sequences of SEQ ID NOS: 1-80, or a complement thereof.

The allele-specific polynucleotide refers to a polynucleotide specifically hybridized with each allele. That is, the allele-specific polynucleotide has the ability that distinguishes nucleotides of polymorphic sites within the polymorphic sequences of SEQ ID NOS: 1-80 and specifically hybridizes with each of the nucleotides. The hybridization is performed under stringent conditions, for example, conditions of 1 M or less in salt concentration and 25° C. or more in temperature. For example, conditions of 5×SSPE (750 mM NaCl, 50 mM Na Phosphate, 5 mM EDTA, pH 7.4) and 25-30° C. are suitable for allele-specific probe hybridization.

In the present invention, the allele-specific polynucleotide may be a primer. As used herein, the term "primer" refers to a single stranded oligonucleotide that acts as a starting point of template-directed DNA synthesis under appropriate conditions, for example in a buffer containing four different nucleoside triphosphates and polymerase such as DNA or RNA polymerase or reverse transcriptase and an appropriate temperature. The appropriate length of the primer may vary according to the purpose of use, generally 15 to 30 nucleotides. Generally, a shorter primer molecule requires a lower temperature to form a stable hybrid with a template. A primer sequence is not necessarily completely complementary with a template but must be complementary enough to hybridize with the template. Preferably, the 3' end of the primer is aligned with a nucleotide of each polymorphic site (position 101) of SEQ ID NOS: 1-80. The primer is hybridized with a target DNA containing a polymorphic site and starts an allelic amplification in which the primer exhibits complete homology with the target DNA. The primer is used in pair with a second primer hybridizing with an opposite strand. Amplified products are obtained by amplification using the two primers, which means that there is a specific allelic form. The primer of the present invention includes a polynucleotide fragment used in a ligase chain reaction (LCR).

In the present invention, the allele-specific polynucleotide may be a probe. As used herein, the term "probe" refers to a hybridization probe, that is, an oligonucleotide capable of sequence-specifically binding with a complementary strand of a nucleic acid. Such a probe may be a peptide nucleic acid as disclosed in Science 254, 1497-1500 (1991) by Nielsen et al. The probe according to the present invention is an allele-specific probe. In this regard, when there are polymorphic sites in nucleic acid fragments derived from two members of the same species, the probe is hybridized with DNA fragments derived from one member but is not hybridized with DNA fragments derived from the other member. In this case, hybridization conditions should be stringent enough to allow hybridization with only one allele by significant difference in hybridization strength between alleles. Preferably, the central portion of the probe, that is, position 7 for a 15 nucleotide probe, or position 8 or 9 for a 16 nucleotide probe, is aligned with each polymorphic site of the nucleotide sequences of SEQ ID NOS: 1-80. Therefore, there may be caused a significant difference in hybridization between alleles. The probe of the present invention can be used in diagnostic methods for detecting alleles. The diagnostic methods include nucleic acid hybridization-based detection methods, e.g., southern blot. In a case where DNA chips are used for the nucleic acid hybridization-based detection methods, the probe may be provided as an immobilized form on a substrate of a DNA chip.

The present invention also provides a microarray for diagnosis of type II diabetes mellitus, including the polynucleotide according to the present invention or the complementary polynucleotide thereof. The polynucleotide of the microarray may be DNA or RNA. The microarray is the same as a common microarray except that it includes the polynucleotide of the present invention.

The present invention also provides a type II diabetes mellitus diagnostic kit including the polynucleotide of the present invention. The type II diabetes mellitus diagnostic kit may include reagents necessary for polymerization, e.g., dNTPs, various polymerases, and a colorant, in addition to the polynucleotide according to the present invention.

The present invention also provides a method of diagnosing type II diabetes mellitus in an individual, which includes: isolating a nucleic acid sample from the individual; and determining a nucleotide of at least one polymorphic site (position 101) within polynucleotides of SEQ ID NOS: 1-80 or complementary polynucleotides thereof. Here, when the nucleotide of the at least one polymorphic site of the sample nucleic acid is the same as at least one risk allele presented in Tables 1-1, 1-2, 2-1, and 2-2, it may be determined that the individual has a higher likelihood of being diagnosed as at risk of developing type II diabetes mellitus.

The step of isolating the nucleic acid sample from the individual may be carried out by a common DNA isolation method. For example, the nucleic acid sample can be obtained by amplifying a target nucleic acid by polymerase chain reaction (PCR) followed by purification. In addition to PCR, there may be used LCR (Wu and Wallace, *Genomics* 4, 560 (1989), Landegren et al., *Science* 241, 1077 (1988)), transcription amplification (Kwoh et al., *Proc. Natl. Acad. Sci. USA* 86, 1173 (1989)), self-sustained sequence replication (Guatelli et al., *Proc. Natl. Acad. Sci. USA* 87, 1874 (1990)), or nucleic acid sequence based amplification (NASBA). The last two methods are related with isothermal reaction based on isothermal transcription and produce 30 or 100-fold RNA single strands and DNA double strands as amplification products.

According to an embodiment of the present invention, the step of determining a nucleotide of a polymorphic site includes hybridizing the nucleic acid sample onto a microarray on which polynucleotides for diagnosis or treatment of type II diabetes mellitus, including at least 10 contiguous nucleotides derived from the group consisting of nucleotide sequences of SEQ ID NOS: 1-80 and including a nucleotide of a polymorphic site (position 101), or complementary polynucleotides thereof are immobilized; and detecting the hybridization result.

A microarray and a method of preparing a microarray by immobilizing a probe polynucleotide on a substrate are well known in the pertinent art. Immobilization of a probe polynucleotide associated with type II diabetes mellitus of the present invention on a substrate can be easily performed using a conventional technique. Hybridization of nucleic acids on a microarray and detection of the hybridization result are also well known in the pertinent art. For example, the detection of the hybridization result can be performed by labeling a nucleic acid sample with a labeling material generating a detectable signal, such as a fluorescent material (e.g., Cy3 and Cy5), hybridizing the labeled nucleic acid sample onto a microarray, and detecting a signal generated from the labeling material.

According to another embodiment of the present invention, as a result of the determination of a nucleotide sequence of a polymorphic site, when at least one nucleotide sequence selected from SEQ ID NOS: 2. 4, 5, 8, 9, 11, 13, 16, 18, 20, 21, 23, 25, 27, 30, 32, 33, 36, 38, 40, 42, 44, 46, 47, 49, 51, 53, 55, 57, 59, 62, 63, 65, 67, 69, 71, 75, 77, and 80 containing risk alleles is detected, it may be determined that the individual has a higher likelihood of being diagnosed as at risk of developing type II diabetes mellitus. If more nucleotide sequences containing risk alleles are detected in an individual, it may be determined that the individual has a much higher likelihood of being diagnosed as at risk of developing type II diabetes mellitus.

Hereinafter, the present invention will be described more specifically by Example. However, the following Example is provided only for illustrations and thus the present invention is not limited thereto.

EXAMPLE

Example 1

In this Example, DNA samples were extracted from blood streams of a patient group consisting of 300 Korean persons that had been identified as type II diabetes mellitus patients and had been being under treatment and a normal group consisting of 300 persons free from symptoms of type II diabetes mellitus and being of the same age with the patient group, and occurrence frequencies of specific SNPs were evaluated. The SNPs were selected from a known database (NCBI Single Nucleotide Polymorphism data base or SEQUENOM RealSNP™ Assay Database). Primers hybridizing with sequences around the selected SNPs were used to assay the nucleotide sequences of SNPs in the DNA samples.

1. Preparation of DNA Samples

DNA samples were extracted from blood streams of type II diabetes mellitus patients and normal persons. DNA extraction was performed according to a known extraction method (Molecular cloning: A Laboratory Manual, p 392, Sambrook, Fritsch and Maniatis, 2nd edition, Cold Spring Harbor Press, 1989) and the specification of a commercial kit manufactured by Centra system. Among extracted DNA samples, only DNA samples having a purity ($A_{260}/A_{280}$ nm) of at least 1.7 were used.

2. Amplification of Target DNAs

Target DNAs, which are predetermined DNA regions containing SNPs to be analyzed, were amplified by PCR. The PCR was performed by a common method as the following conditions. First, 2.5 ng/ml of target genomic DNAs were prepared. Then, the following PCR mixture was prepared.

| | |
|---|---|
| Water (HPLC grade) | 2.24 µl |
| 10x buffer (15 mM $MgCl_2$, 25 mM $MgCl_2$) | 0.5 µl |
| dNTP Mix (GIBCO) (25 mM for each) | 0.04 µl |
| Taq pol (HotStar) (5 U/µl) | 0.02 µl |
| Forward/reverse primer Mix (1 µM for each) | 0.02 µl |
| DNA | 1.00 µl |
| Total volume | 5.00 µl |

Here, the forward and reverse primers were designed based on upstream and downstream sequences of SNPs in known database. These primers are listed in Table 3 below.

The thermal cycles of PCR were as follows: incubation at 95° C. for 15 minutes; 45 cycles at 95° C. for 30 seconds, at 56° C. for 30 seconds, and at 72° C. for 1 minute; and incubation at 72° C. for 3 minutes and storage at 4° C. As a result, amplified DNA fragments which were 200 or less nucleotides in length were obtained.

3. Analysis of SNPs in Amplified Target DNA Fragments

Analysis of SNPs in the amplified target DNA fragments was performed using a homogeneous MassExtension (hME) technique available from Sequenom. The principle of the MassExtension technique was as follows. First, primers (also called as "extension primers") ending immediately before SNPs within the target DNA fragments were designed. Then, the primers were hybridized with the target DNA fragments and DNA polymerization was performed. At this time, a polymerization solution contained a reagent (e.g., ddTTP) terminating the polymerization immediately after the incorporation of a nucleotide complementary to a first allelic nucleotide (e.g., A allele). In this regard, when the first allele (e.g., A allele) exists in the target DNA fragments, products in which only a nucleotide (e.g., T nucleotide) complementary to the first allele extended from the primers will be obtained. On the other hand, when a second allele (e.g., G allele) exists in the target DNA fragments, a nucleotide (e.g., C nucleotide) complementary to the second allele is added to the 3'-ends of the primers and then the primers are extended until a nucleotide complementary to the closest first allele nucleotide (e.g., T nucleotide) is added. The lengths of products extended from the primers were determined by mass spectrometry. Therefore, alleles present in the target DNA fragments could be identified. Illustrative experimental conditions were as follows.

First, unreacted dNTPs were removed from the PCR products. For this, 1.53 μl of deionized water, 0.17 μl of HME buffer, and 0.30 μl of shrimp alkaline phosphatase (SAP) were added and mixed in 1.5 ml tubes to prepare SAP enzyme solutions. The tubes were centrifuged at 5,000 rpm for 10 seconds. Thereafter, the PCR products were added to the SAP solution tubes, sealed, incubated at 37° C. for 20 minutes and then 85° C. for 5 minutes, and stored at 4° C.

Next, homogeneous extension was performed using the amplified target DNA fragments as templates. The compositions of the reaction solutions for the extension were as follows.

| | |
|---|---|
| Water (nanoscale deionized water) | 1.728 μl |
| hME extension mix (10x buffer containing 2.25 mM d/ddNTPs) | 0.200 μl |
| Extension primers (100 μM for each) | 0.054 μl |
| Thermosequenase (32 U/μl) | 0.018 μl |
| Total volume | 2.00 μl |

The reaction solutions were thoroughly mixed with the previously prepared target DNA solutions and subjected to spin-down centrifugation. Tubes or plates containing the reaction solutions were compactly sealed and incubated at 94° C. for 2 minutes, followed by homogeneous extension for 40 cycles at 94° C. for 5 seconds, at 52° C. for 5 seconds, and at 72° C. for 5 seconds, and storage at 4° C. The homogeneous extension products thus obtained were washed with a resin (SpectroCLEAN). Extension primers used in the extension are listed in Table 3 below.

TABLE 3

Primers for amplification and extension primers for homogeneous extension for target DNAs

| Marker | Amplification primer (SEQ ID NO) | | Extension primer (SEQ ID NO) |
|---|---|---|---|
| | Forward primer | Reverse primer | |
| DMX_001 | 81 | 82 | 83 |
| DMX_003 | 84 | 85 | 86 |
| DMX_005 | 87 | 88 | 89 |
| DMX_008 | 90 | 91 | 92 |
| DMX_009 | 93 | 94 | 95 |
| DMX_011 | 96 | 97 | 98 |
| DMX_012 | 99 | 100 | 101 |
| DMX_014 | 102 | 103 | 104 |
| DMX_016 | 105 | 106 | 107 |
| DMX_019 | 108 | 109 | 110 |
| DMX_027 | 111 | 112 | 113 |
| DMX_028 | 114 | 115 | 116 |
| DMX_029 | 117 | 118 | 119 |
| DMX_030 | 120 | 121 | 122 |
| DMX_031 | 123 | 124 | 125 |
| DMX_032 | 126 | 127 | 128 |
| DMX_033 | 129 | 130 | 131 |
| DMX_044 | 132 | 133 | 134 |
| DMX_049 | 135 | 136 | 137 |
| DMX_052 | 138 | 139 | 140 |
| DMX_054 | 141 | 142 | 143 |
| DMX_056 | 144 | 145 | 146 |
| DMX_060 | 147 | 148 | 149 |
| DMX_061 | 150 | 151 | 152 |
| DMX_062 | 153 | 154 | 155 |
| DMX_063 | 156 | 157 | 158 |
| DMX_065 | 159 | 160 | 161 |
| DMX_067 | 162 | 163 | 164 |
| DMX_068 | 165 | 166 | 167 |

TABLE 3-continued

Primers for amplication and extension primers for homogeneous extension for target DNAs

| Marker | Amplification primer (SEQ ID NO) | | Extension primer (SEQ ID NO) |
|---|---|---|---|
| | Forward primer | Reverse primer | |
| DMX_069 | 168 | 169 | 170 |
| DMX_104 | 171 | 172 | 173 |
| DMX_105 | 174 | 175 | 176 |
| DMX_116 | 177 | 178 | 179 |
| DMX_117 | 180 | 181 | 182 |
| DMX_120 | 183 | 184 | 185 |
| DMX_136 | 186 | 187 | 188 |
| DMX_139 | 189 | 190 | 191 |
| DMX_150 | 192 | 193 | 194 |
| DMX_152 | 195 | 196 | 197 |
| DMX_154 | 198 | 199 | 200 |

Nucleotides of polymorphic sites in the extension products were assayed using mass spectrometry, MALDI-TOF (Matrix Assisted Laser Desorption and Ionization-Time of Flight). The MALDI-TOF is operated according to the following principle. When an analyte is exposed to a laser beam, it flies toward a detector positioned at the opposite side in a vacuum state, together with an ionized matrix. At this time, the time taken for the analyte to reach the detector is calculated. A material with a smaller mass reaches the detector more rapidly. The nucleotides of SNPs in the target DNA fragments are determined based on a difference in mass between the DNA fragments and known nucleotide sequences of the SNPs.

Determination results of the nucleotides of polymorphic sites of the target DNAs using the MALDI-TOF are shown in Tables 1-1, 1-2, 2-1, and 2-2. Each allele may exist in the form of homozygote or heterozygote in an individual. However, the distribution between heterozygotes frequency and homozygotes frequency in a given population does not exceed a statistically significant level. According to Mendel's Law of inheritance and Hardy-Weinberg Law, a genetic makeup of alleles constituting a population is maintained at a constant frequency. When the genetic makeup is statistically significant, it can be considered to be biologically meaningful. The SNPs according to the present invention occur in type II diabetes mellitus patients at a statistically significant level, as shown in Tables 1-1, 1-2, 2-1, and 2-2, and thus, can be efficiently used in diagnosis of type II diabetes mellitus.

The polynucleotide according to the present invention can be used in diagnosis, treatment, or fingerprinting analysis of type II diabetes mellitus.

The microarray and diagnostic kit including the polynucleotide according to the present invention can be used for efficient diagnosis of type II diabetes mellitus.

The method of analyzing polynucleotides associated with type II diabetes mellitus according to the present invention can efficiently detect the presence or a risk of type II diabetes mellitus.

The invention claimed is:

1. A method for determining increased risk of developing type II diabetes mellitus in a human comprising:
   determining the nucleotide at a polymorphic site at position 101 of SEQ ID NO: 23 in a nucleic acid sample from the human is thymine (T), and
   determining the human has an increased risk of developing type II diabetes mellitus.

2. The method of claim 1, wherein determining the nucleotide of the polymorphic site comprises:
   hybridizing the nucleic acid sample onto a microarray on which is immobilized a polynucleotide comprising
   (a) at least 10 contiguous nucleotides of SEQ ID NO: 23 which comprise position 101, or
   (b) the complement of (a); and
   detecting a hybridization result.

3. The method of claim 1, further comprising:
   determining the genotype in the nucleic acid sample at the polymorphic site is TC, and determining the human has an increased risk of developing type II diabetes as compared to determining the genotype is CC.

* * * * *